(12) United States Patent
Sourov

(10) Patent No.: US 12,210,667 B2
(45) Date of Patent: Jan. 28, 2025

(54) MEDICAL IMAGE OVERLAYS FOR AUGMENTED REALITY EXPERIENCES

(71) Applicant: Alexander Sourov, Seattle, WA (US)

(72) Inventor: Alexander Sourov, Seattle, WA (US)

(73) Assignee: Snap Inc., Santa Monica, CA (US)

( * ) Notice: Subject to any disclaimer, the term of this patent is extended or adjusted under 35 U.S.C. 154(b) by 126 days.

(21) Appl. No.: 17/882,158

(22) Filed: Aug. 5, 2022

(65) Prior Publication Data
US 2024/0045491 A1 Feb. 8, 2024

(51) Int. Cl.
*G06F 3/01* (2006.01)
*G02B 27/01* (2006.01)
*G06T 19/00* (2011.01)

(52) U.S. Cl.
CPC .......... *G06F 3/011* (2013.01); *G02B 27/0172* (2013.01); *G06T 19/006* (2013.01); *G02B 2027/0138* (2013.01)

(58) Field of Classification Search
CPC ..... G06F 3/011; G06F 3/012; G02B 27/0172; G02B 2027/0138; G06T 19/006; G06T 11/00; G16H 30/20; G16H 30/40; G16H 40/63
See application file for complete search history.

(56) References Cited

U.S. PATENT DOCUMENTS

| | | |
|---|---|---|
| 11,277,597 B1 | 3/2022 | Canberk et al. |
| 2014/0275760 A1 | 9/2014 | Lee et al. |
| 2015/0058023 A1 | 2/2015 | Goo |
| 2018/0185100 A1* | 7/2018 | Weinstein ............. A61F 2/461 |
| 2019/0302460 A1* | 10/2019 | Kaul ..................... G10L 15/00 |
| 2019/0324530 A1 | 10/2019 | Stellmach et al. |
| 2020/0221155 A1 | 7/2020 | Hansen et al. |
| 2020/0342228 A1 | 10/2020 | Prevrhal et al. |
| 2021/0121271 A1 | 4/2021 | Kopelman et al. |

(Continued)

FOREIGN PATENT DOCUMENTS

| | | |
|---|---|---|
| KR | 102067089 B1 | 1/2020 |
| WO | 2022035110 A1 | 2/2022 |

OTHER PUBLICATIONS

Bichlmeier, Christoph, et al. "Contextual anatomic mimesis hybrid in-situ visualization method for improving multi-sensory depth perception in medical augmented reality." 2007 6th IEEE and ACM international symposium on mixed and augmented reality. IEEE, 2007. (Year: 2007).*

(Continued)

*Primary Examiner* — Daniel F Hajnik
(74) *Attorney, Agent, or Firm* — CM Law; Stephen J. Weed

(57) ABSTRACT

A medical image overlay application for use with augmented reality (AR) eyewear devices. The image overlay application enables a user of an eyewear device to activate an image overlay on a display when the eyewear device detects that the camera field of view includes a medical image location. Medical image locations are defined relative to virtual markers. The image overlay includes one or more medical images, presented according to a configurable transparency value. An image registration tool transforms the location and scale of each medical image to the physical environment, such that the medical image as presented on the display closely matches the location and size of real objects.

13 Claims, 15 Drawing Sheets

(56) References Cited

U.S. PATENT DOCUMENTS

| | | |
|---|---|---|
| 2021/0224031 A1 | 7/2021 | Nair et al. |
| 2021/0375048 A1 | 12/2021 | Kang et al. |
| 2021/0407203 A1 | 12/2021 | Canberk et al. |
| 2022/0108696 A1 | 4/2022 | van Scheltinga et al. |
| 2022/0168044 A1 | 6/2022 | Oliveira |
| 2022/0244786 A1 | 8/2022 | Chu et al. |

OTHER PUBLICATIONS

NPL Video Titled: "Augmented Reality for Spine Surgery", available for viewing at: https://www.youtube.com/watch?v=RNE8jPlti-E ; Published by "Ivanhoe Web" on Oct. 12, 2020; select screenshots included. (Year: 2020).*

International Search Report and Written Opinion for International Application No. PCT/US2023/028171, dated Nov. 21, 2023 (Nov. 21, 2023)—9 pages.

International Search Report and Written Opinion for International Application No. PCT/US2023/028251, dated Jul. 20, 2023 (Jul. 20, 2023)—8 pages.

* cited by examiner

US 12,210,667 B2

MEDICAL IMAGE OVERLAYS FOR AUGMENTED REALITY EXPERIENCES

TECHNICAL FIELD

Examples set forth in the present disclosure relate to the field of augmented reality (AR) experiences for electronic devices, including wearable devices such as eyewear devices. More particularly, but not by way of limitation, the present disclosure describes the registration and presentation of medical images on the display of eyewear devices.

BACKGROUND

Many types of computers and electronic devices available today, such as mobile devices (e.g., smartphones, tablets, and laptops), handheld devices, and wearable devices (e.g., smart glasses, digital eyewear, headwear, headgear, and head-mounted displays), include a variety of cameras, sensors, wireless transceivers, input systems, and displays. Users sometimes refer to information on these devices during physical activities such as exercise.

Virtual reality (VR) technology generates a complete virtual environment including realistic images, sometimes presented on a VR headset or other head-mounted display. VR experiences allow a user to move through the virtual environment and interact with virtual objects. AR is a type of VR technology that combines real objects in a physical environment with virtual objects and displays the combination to a user. The combined display gives the impression that the virtual objects are authentically present in the environment, especially when the virtual objects appear and behave like the real objects. Cross reality (XR) is generally understood as an umbrella term referring to systems that include or combine elements from AR, VR, and MR (mixed reality) environments.

Automatic speech recognition (ASR) is a field of computer science, artificial intelligence, and linguistics which involves receiving spoken words and converting the spoken words into audio data suitable for processing by a computing device. Processed frames of audio data can be used to translate the received spoken words into text or to convert the spoken words into commands for controlling and interacting with various software applications. ASR processing may be used by computers, handheld devices, wearable devices, telephone systems, automobiles, and a wide variety of other devices to facilitate human-computer interactions.

BRIEF DESCRIPTION OF THE DRAWINGS

Features of the various examples described will be readily understood from the following detailed description, in which reference is made to the figures. A reference numeral is used with each element in the description and throughout the several views of the drawing. When a plurality of similar elements is present, a single reference numeral may be assigned to like elements, with an added upper or lower-case letter referring to a specific element.

The various elements shown in the figures are not drawn to scale unless otherwise indicated. The dimensions of the various elements may be enlarged or reduced in the interest of clarity. The several figures depict one or more implementations and are presented by way of example only and should not be construed as limiting. Included in the drawing are the following figures.

DETAILED DESCRIPTION

Figure 1A:
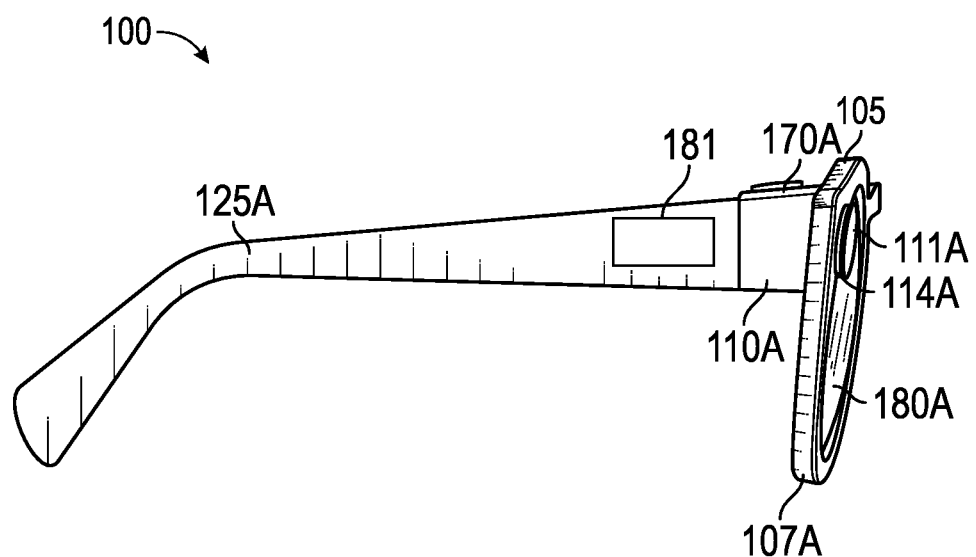
FIG. 1A is a side view (right) of an eyewear device suitable for use in an example virtual guided fitness system.

An overlay application for use with AR eyewear devices. The application enables a user of an eyewear device to view a medical image (e.g., a radiograph image of a target of interest, such as a tooth) presented as an overlay relative to the target. An image registration tool transforms the location, rotation, and scale of the original medical image so that the image overlay is closely aligned with the target, as viewed through the eyewear display, from any point of view.

Various implementations and details are described with reference to examples for presenting a medical image overlay in an augmented reality environment. In an example implementation, a method involves an eyewear device with a camera and display and includes storing a virtual marker including a marker location defined relative to a physical environment, and registering a medical image associated with a target, wherein the medical image includes an image location defined relative to the marker location. The method also includes determining a current eyewear device location relative to the marker location based on the frames of video data captured using the camera and presenting on the display a medical image overlay at the image location according to the current eyewear device location. The medical image overlay includes one or more of the registered medical images, presented on the display according to a transparency value. The medical image overlay, including the transparency value, can be adjusted and controlled using voice commands, gestures, or inputs to a touchpad.

In another example implementation, the method includes selectively presenting a medical image overlay that includes a plurality of medical images. In this example, the method includes determining, based on the captured frames of video data, whether a medical image location is detected within the field of view of the camera and, in response, selectively presenting the medical image associated with the detected image location.

Although the various systems and methods are described herein with reference to dental procedures, the technology described herein may be applied to essentially any type of activity or work in which an image overlay is desired. For example, an image overlay is a desired tool for activities like dentistry, medical examinations, surgery, industrial applications, quality control activities, inspections, surveys, and investigations of all kinds.

The following detailed description includes systems, methods, techniques, instruction sequences, and computer program products illustrative of examples set forth in the disclosure. Numerous details and examples are included for the purpose of providing a thorough understanding of the disclosed subject matter and its relevant teachings. Those skilled in the relevant art, however, may understand how to apply the relevant teachings without such details. Aspects of the disclosed subject matter are not limited to the specific devices, systems, and methods described because the relevant teachings can be applied or practiced in a variety of ways. The terminology and nomenclature used herein is for the purpose of describing particular aspects only and is not intended to be limiting. In general, well-known instruction instances, protocols, structures, and techniques are not necessarily shown in detail.

The term "connect," "connected," "couple," and "coupled" as used herein refers to any logical, optical, physical, or electrical connection, including a link or the like by which the electrical or magnetic signals produced or supplied by one system element are imparted to another coupled or connected system element. Unless described otherwise, coupled, or connected elements or devices are not necessarily directly connected to one another and may be separated by intermediate components, elements, or communication media, one or more of which may modify, manipulate, or carry the electrical signals. The term "on" means directly supported by an element or indirectly supported by the element through another element integrated into or supported by the element.

The term "proximal" is used to describe an item or part of an item that is situated near, adjacent, or next to an object or person; or that is closer relative to other parts of the item, which may be described as "distal." For example, the end of an item nearest an object may be referred to as the proximal end, whereas the generally opposing end may be referred to as the distal end.

The orientations of the eyewear device, associated components and any complete devices incorporating an eye scanner and camera such as shown in any of the drawings, are given by way of example only, for illustration and discussion purposes. In operation for a particular variable optical processing application, the eyewear device may be oriented in any other direction suitable to the particular application of the eyewear device, for example up, down, sideways, or any other orientation. Also, to the extent used herein, any directional term, such as front, rear, inwards, outwards, towards, left, right, lateral, longitudinal, up, down, upper, lower, top, bottom and side, are used by way of example only, and are not limiting as to direction or orientation of any optic or component of an optic constructed as otherwise described herein.

Advanced AR technologies, such as computer vision and object tracking, may be used to produce a perceptually enriched and immersive experience. Computer vision algorithms extract three-dimensional data about the physical world from the data captured in digital images or video. Object recognition and tracking algorithms are used to detect an object in a digital image or video, estimate its orientation or pose, and track its movement over time.

Additional objects, advantages and novel features of the examples will be set forth in part in the following description, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

In sample configurations, eyewear devices with augmented reality (AR) capability are used in the systems described herein. Eyewear devices are desirable to use in the system described herein as such devices are scalable, customizable to enable personalized experiences, enable effects to be applied anytime, anywhere, and ensure user privacy by enabling only the user to see the transmitted information. An eyewear device such as SPECTACLES™ available from Snap, Inc. of Santa Monica, California, may be used without any specialized hardware in a sample configuration.

As shown in FIGS. 1A-1D, the eyewear device 100 includes a first camera 114A and a second camera 114B. The cameras 114 capture image information for a scene from separate viewpoints. The captured images may be used to project a three-dimensional display onto an image display for three dimensional (3D) viewing.

Figure 3:
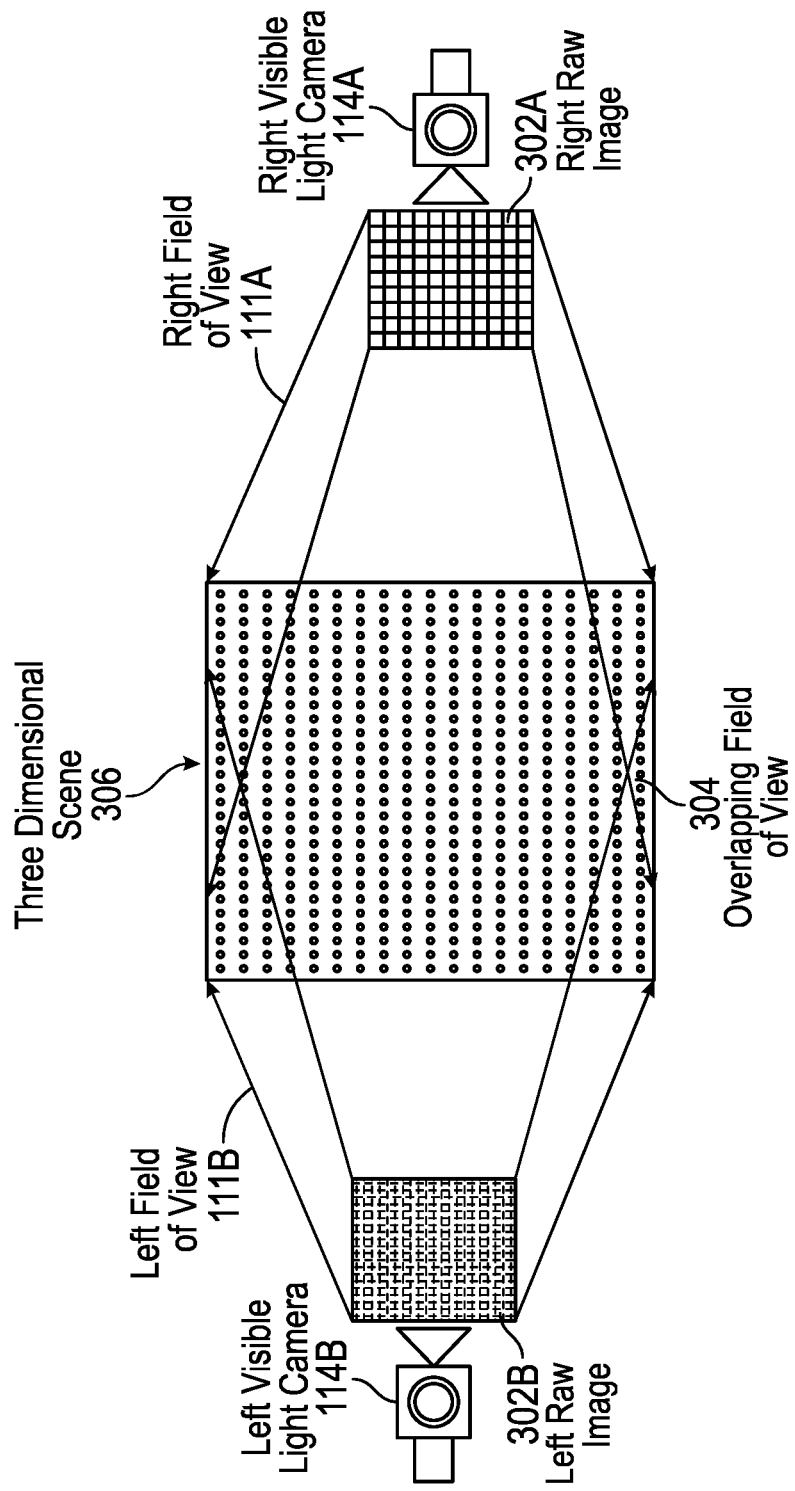
FIG. 3 is a block diagram illustrating an example of capturing visible light using an example eyewear device illustrated in any of the proceeding figures.

The cameras 114 are sensitive to the visible-light range wavelength. Each of the cameras 114 define a different frontward facing field of view, which are overlapping to enable generation of 3D depth images; for example, a first camera 114A defines a first field of view 111A and a second camera 114B defines a second field of view 111B. Generally, a "field of view" is the part of the scene that is visible through the camera at a particular position and orientation in space. The fields of view 111 have an overlapping field of view 304 (FIG. 3). Objects or object features outside the field of view 111 when the camera captures the image are not recorded in a raw image (e.g., photograph or picture). The field of view describes an angle range or extent, which the image sensor of the camera 114 picks up electromagnetic radiation of a given scene in a captured image of the given scene. Field of view can be expressed as the angular size of the view cone; i.e., an angle of view. The angle of view can be measured horizontally, vertically, or diagonally.

In an example configuration, one or both cameras 114 has a field of view of 100° and a resolution of 480×480 pixels. The "angle of coverage" describes the angle range that a lens of the cameras 114 can effectively image. Typically, the camera lens produces an image circle that is large enough to cover the film or sensor of the camera completely, possibly including some vignetting (e.g., a darkening of the image toward the edges when compared to the center). If the angle of coverage of the camera lens does not fill the sensor, the image circle will be visible, typically with strong vignetting toward the edge, and the effective angle of view will be limited to the angle of coverage.

Examples of suitable cameras 114 include a high-resolution complementary metal-oxide-semiconductor (CMOS) image sensor and a digital VGA camera (video graphics array) capable of resolutions of 480p (e.g., 640×480 pixels), 720p, 1080p, or greater. Other examples include cameras 114 that can capture high-definition (HD) video at a high frame rate (e.g., thirty to sixty frames per second, or more) and store the recording at a resolution of 1216 by 1216 pixels (or greater).

The eyewear device 100 may capture image sensor data from the cameras 114 along with geolocation data, digitized by an image processor, for storage in a memory. The cameras 114 capture respective raw images (e.g., left and right raw images) in the two-dimensional space domain that comprise a matrix of pixels on a two-dimensional coordinate system that includes an X-axis for horizontal position and a Y-axis for vertical position. Each pixel includes a color attribute value (e.g., a red pixel light value, a green pixel light value, or a blue pixel light value); and a position attribute (e.g., an X-axis coordinate and a Y-axis coordinate).

In order to capture stereo images for later display as a 3D projection, the image processor 412 (FIG. 4) may be coupled to the cameras 114 to receive and store the visual image information. The image processor 412, or another processor, controls operation of the cameras 114 to act as a stereo camera simulating human binocular vision and may add a timestamp to each image. The timestamp on each pair of images allows display of the images together as part of a 3D projection. 3D projections produce an immersive, life-like experience that is desirable in a variety of contexts, including virtual reality (VR) and video gaming.

Figure 1B:
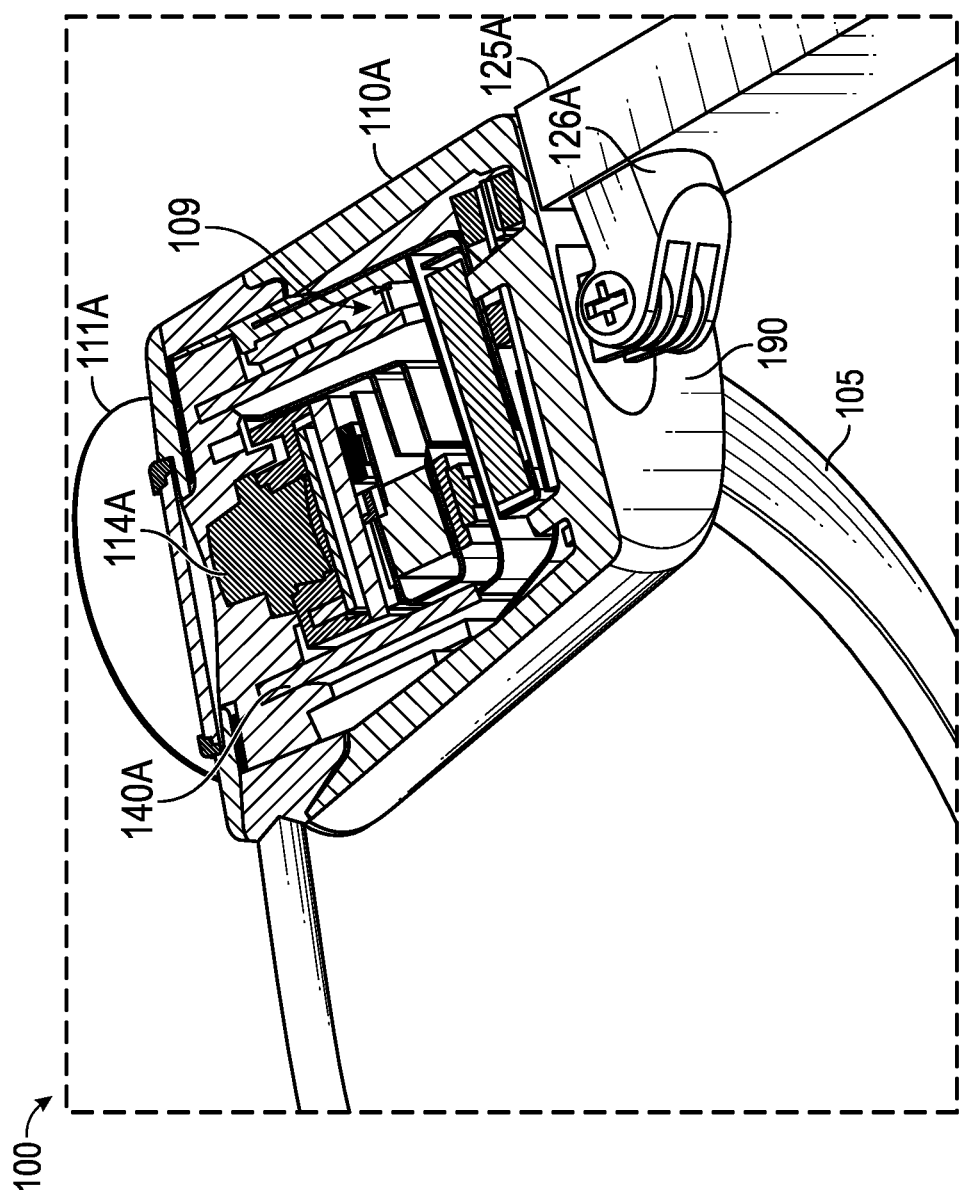
FIG. 1B is a perspective, partly sectional view of optical components and electronics in a portion of the eyewear device illustrated in FIG. 1A.
Figure 1C:
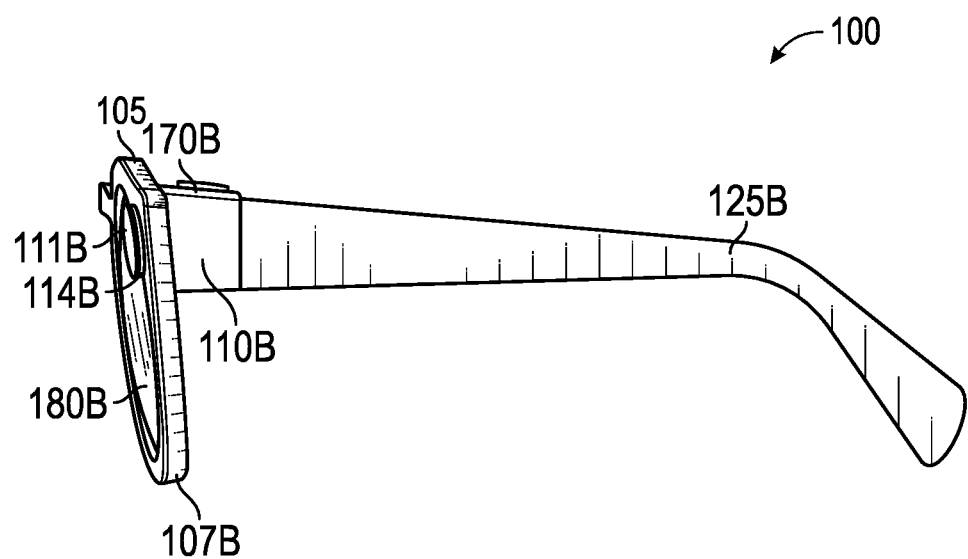
FIG. 1C is a side view (left) of the eyewear device of FIG. 1A.
Figure 1D:
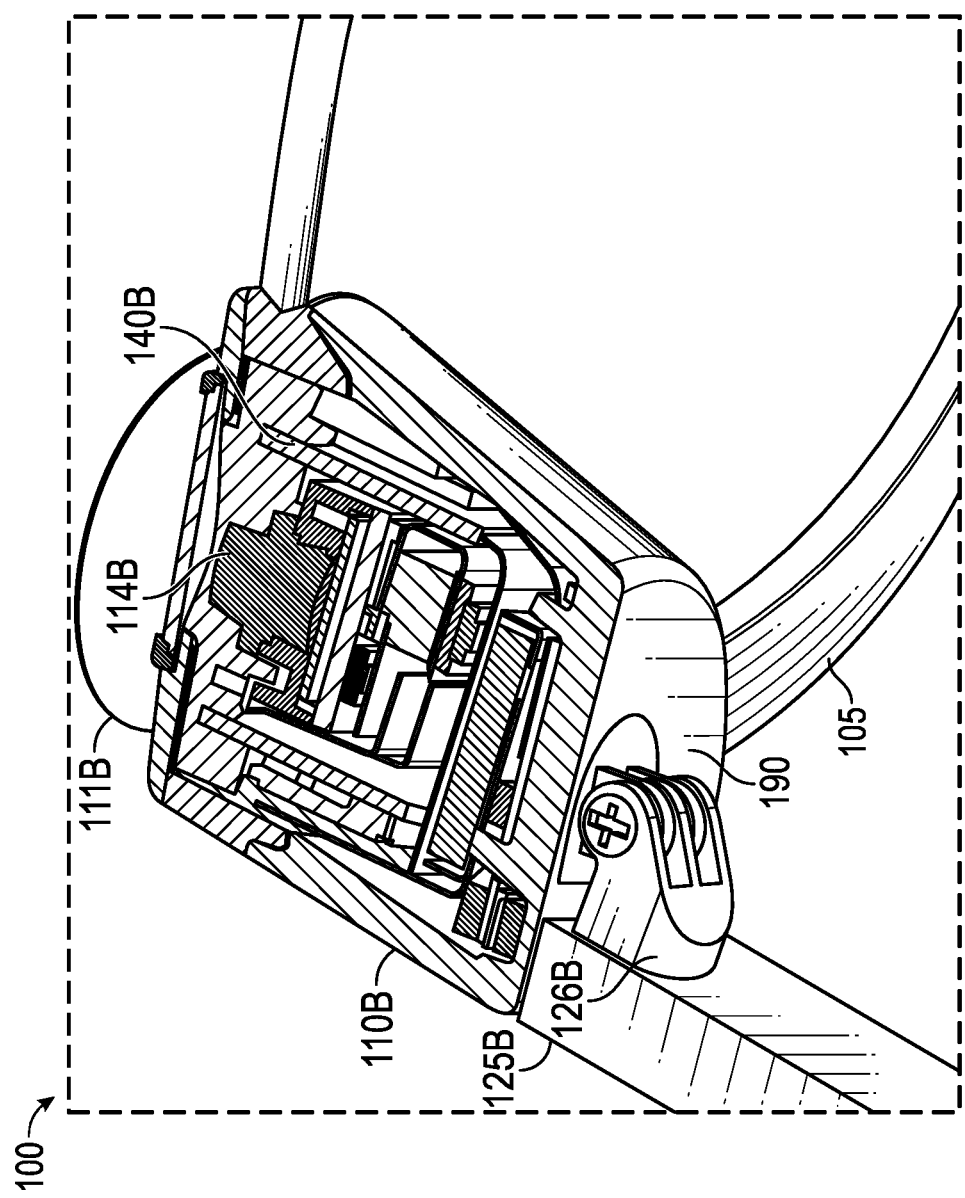
FIG. 1D is a perspective, partly sectional view of optical components and electronics in a portion of the eyewear device illustrated in FIG. 1C.

FIG. 1B is a perspective, cross-sectional view of a right corner 110A of the eyewear device 100 of FIG. 1A depicting the first camera 114A, additional optical components, and electronics. FIG. 1C is a side view (left) of an example hardware configuration of an eyewear device 100 of FIG. 1A, which shows the second camera 114B of the camera system. FIG. 1D is a perspective, cross-sectional view of a left corner 110B of the eyewear device 100 of FIG. 1C depicting the second camera 114B of the camera system, additional optical components, and electronics.

As shown in the example of FIG. 1B, the eyewear device 100 includes the first camera 114A and a circuit board 140A, which may be a flexible printed circuit board (PCB). A first hinge 126A connects the right corner 110A to a first temple 125A of the eyewear device 100. In some examples, components of the first camera 114A, the flexible PCB 140A, or other electrical connectors or contacts may be located on the first temple 125A or the first hinge 126A.

The right corner 110A includes corner body 190 and a corner cap, with the corner cap omitted in the cross-section of FIG. 1B. Disposed inside the right corner 110A are various interconnected circuit boards 109, such as the flexible PCB 140A, that include controller circuits for the first camera 114A, microphone(s) 139, speaker(s) 191, low-power wireless circuitry (e.g., for wireless short range network communication via Bluetooth™), high-speed wireless circuitry (e.g., for wireless local area network communication via Wi-Fi).

Figure 2A:
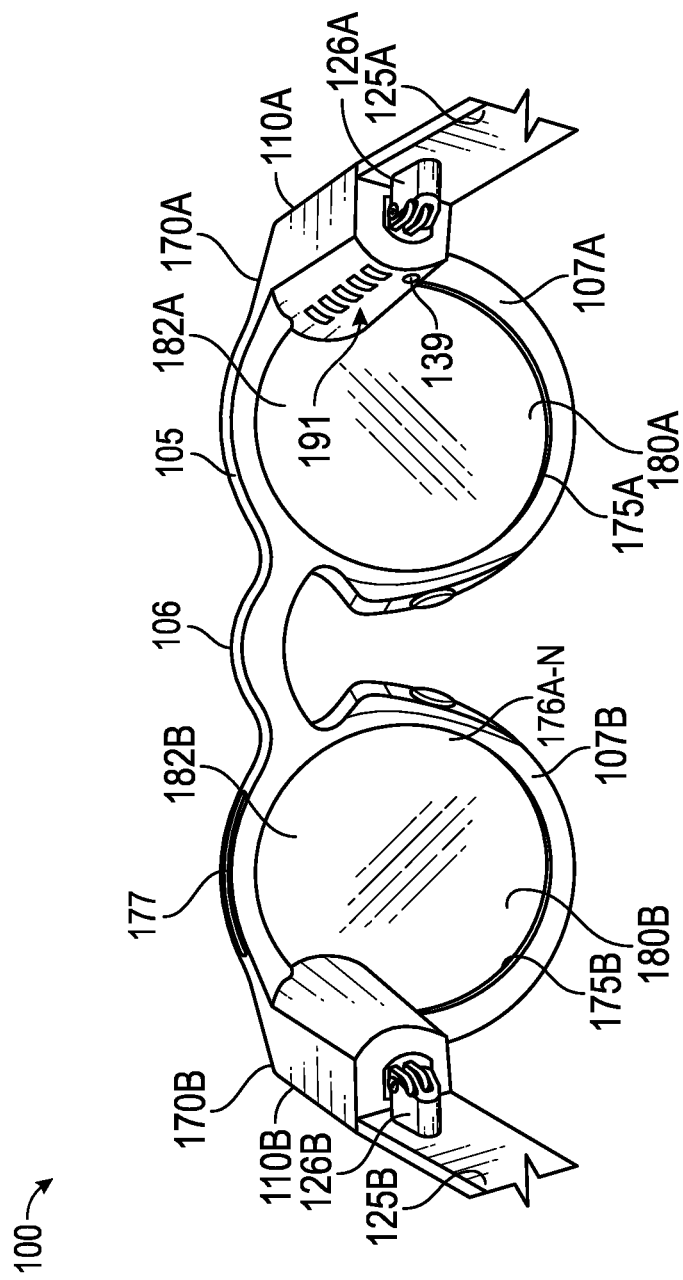
FIGS. 2A and 2B are rear views of an eyewear device utilized in an example virtual guided fitness system.

The first camera 114A is coupled to or disposed on the flexible PCB 140A and is covered by a camera cover lens, which is aimed through opening(s) formed in the frame 105. For example, the right rim 107A of the frame 105, shown in FIG. 2A, is connected to the right corner 110A and includes the opening(s) for the camera cover lens. The frame 105 includes a front side configured to face outward and away from the eye of the user. The opening for the camera cover lens is formed on and through the front or outward-facing side of the frame 105. In the example, the first camera 114A has an outward-facing field of view 111A (shown in FIG. 3) with a line of sight or perspective that is correlated with the right eye of the user of the eyewear device 100. The camera cover lens can also be adhered to a front side or outward-facing surface of the right corner 110A in which an opening is formed with an outward-facing angle of coverage, but in a different outwardly direction. The coupling can also be indirect via intervening components.

As shown in the example of FIG. 1D, the eyewear device 100 includes the second camera 114B and a circuit board 140B, which may be a flexible printed circuit board (PCB). A second hinge 126B connects the left corner 110B to a second temple 125B of the eyewear device 100. In some examples, components of the second camera 114B, the flexible PCB 140B, or other electrical connectors or contacts may be located on the second temple 125B or the second hinge 126B.

The left corner 110B includes corner body 190 and a corner cap, with the corner cap omitted in the cross-section of FIG. 1D. Disposed inside the right corner 110A are various interconnected circuit boards, such as the flexible PCB 140B, that include controller circuits for the second camera 114B.

The camera 114 are coupled to or disposed on respective flexible PCBs 140 and are covered by a camera cover lens, which is aimed through opening(s) formed in the frame 105. For example, as shown in FIG. 2A, the right rim 107A of the frame 105 is connected to the right corner 110A and includes the opening(s) for the camera cover lens and the left rim 107B of the frame 105 is connected to the left corner 110B and includes the opening(s) for the camera cover lens. The frame 105 includes a front side configured to face outward and away from the eye of the user. The opening for the camera cover lens is formed on and through the front or outward-facing side of the frame 105. In the example, the cameras 114 have respective outward-facing fields of view 111 (shown in FIG. 3) with a line of sight or perspective that is correlated with a respective eye of the user of the eyewear device 100. The camera cover lenses can also be adhered to a front side or outward-facing surface of the respective corners 110 in which an opening is formed with an outward-facing angle of coverage, but in a different outwardly direction. The coupling can also be indirect via intervening components.

Figure 2B:
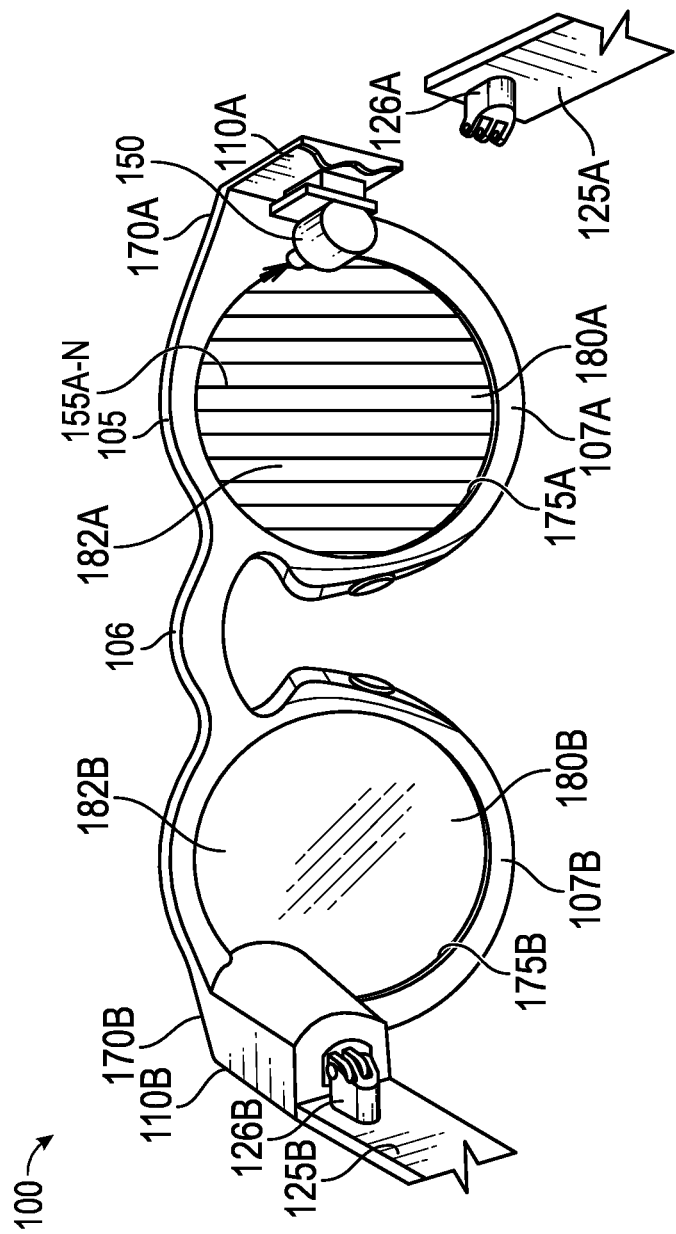

FIGS. 2A and 2B depict example hardware configurations of the eyewear device 100, including two different types of image displays. The eyewear device 100 is sized and shaped in a form configured for wearing by a user. The form of eyeglasses is shown in the illustrated examples. The eyewear device 100 can take other forms and may incorporate other types of frameworks; for example, a headgear, a headset, or a helmet.

In the eyeglasses example, eyewear device 100 includes a frame 105 including a right rim 107A connected to a left rim 107B via a bridge 106 configured to receive a nose of the user to support the eyewear device 100 on the user's head. The right rim 107A includes a first aperture 175A, which holds a first optical element 180A. The left rim 107B includes a second aperture 175B, which holds a second optical element 180B. As shown in FIG. 2B, each optical element 180A, 180B in some implementations includes an integrated image display (e.g., a first display 182A and a second display 182B). As used herein, the term "lens" is meant to include transparent or translucent pieces of glass or plastic having curved or flat surfaces that cause light to converge or diverge or that cause little or no convergence or divergence.

A touch-sensitive input device, such as a touchpad 181 is positioned on the first temple 125A. As shown, the touchpad 181 may have a boundary that is plainly visible or includes a raised or otherwise tactile edge that provides feedback to the user about the location and boundary of the touchpad 181; alternatively, the boundary may be subtle and not easily seen or felt. The eyewear device 100 may include a touchpad on the other side that operates independently or in conjunction with the touchpad 181.

The surface of the touchpad 181 is configured to detect finger touches, taps, and gestures (e.g., moving touches) for use with a graphical user interface (GUI) displayed by the eyewear device, on an image display, to allow the user to navigate through and select menu options in an intuitive manner, which enhances and simplifies the user experience.

Detection of finger inputs on the touchpad 181 can enable several functions. For example, touching anywhere on the touchpad 181 may cause the GUI to display or highlight an item on the image display, which may be projected onto at least one of the optical assemblies 180. Tapping or double tapping on the touchpad 181 may select an item or icon. Sliding or swiping a finger in a particular direction (e.g., from front to back, back to front, up to down, or down to) may cause the items or icons to slide or scroll in a particular direction; for example, to move to a next item, icon, video, image, page, or slide. Sliding the finger in another direction may slide or scroll in the opposite direction; for example, to move to a previous item, icon, video, image, page, or slide. The touchpad 181 can be positioned essentially anywhere on the eyewear device 100.

In one example, an identified finger gesture of a single tap on the touchpad 181, initiates selection or pressing of a GUI element in the image presented on the image display of the optical assembly 180. An adjustment to the image presented on the image display of the optical assembly 180 based on the identified finger gesture can be a primary action which selects or submits the GUI element on the image display of the optical assembly 180 for further display or execution.

FIG. 2A is an example hardware configuration for the eyewear device 100 in which the right corner 110A supports a microphone 139 and a speaker 191. The microphone 139 includes a transducer that converts sound into a corresponding electrical audio signal. The microphone 139 in the illustrated example is positioned with an opening that faces inward toward the wearer, to facilitate reception of the sound waves, such as human speech including verbal commands and questions. Additional or differently oriented openings may be implemented. In other example configurations, the eyewear device 100 is coupled to one or more microphones 139, configured to operate together or independently, and positioned at various locations on the eyewear device 100.

Figure 4:
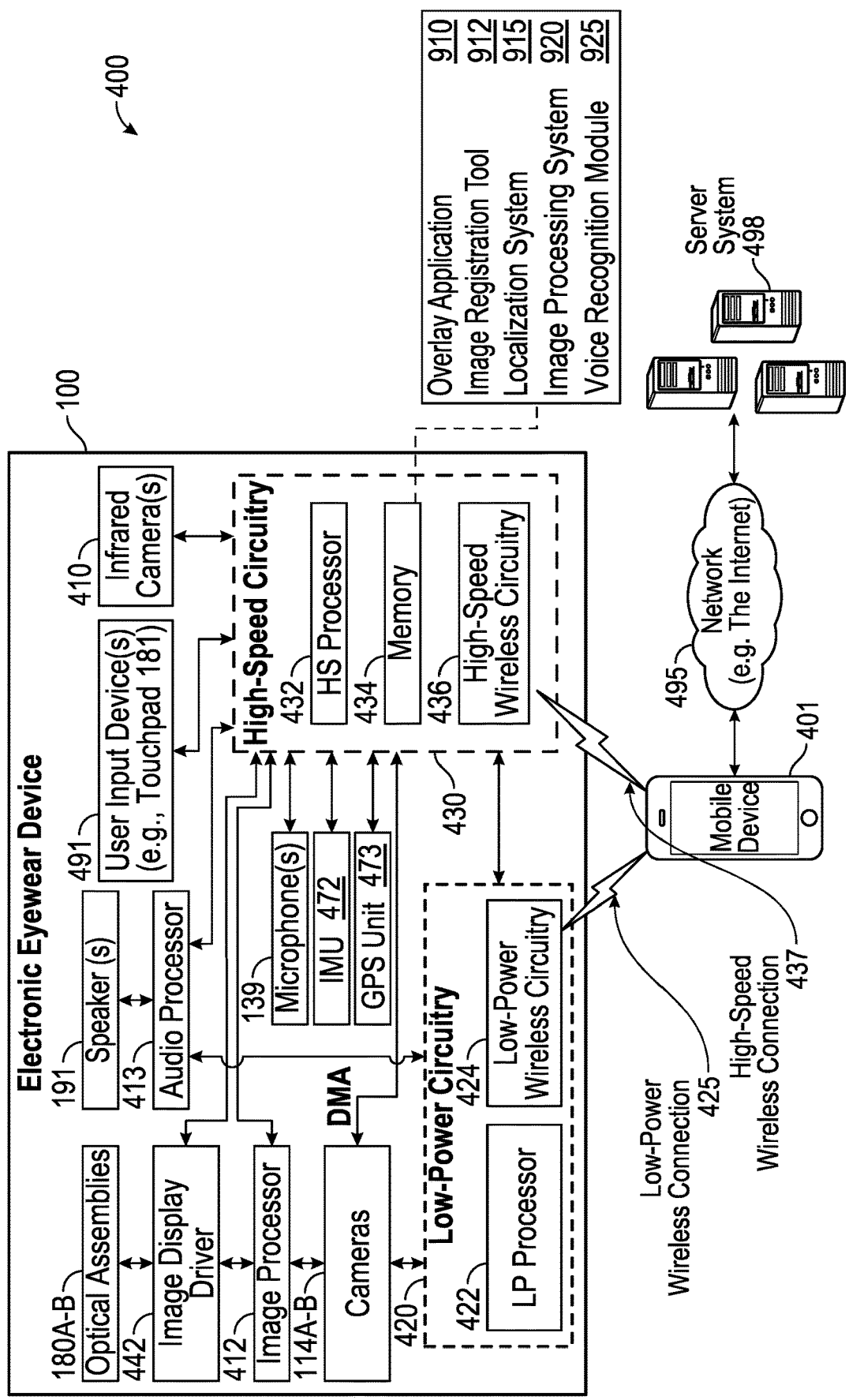
FIG. 4 is a functional block diagram of an example overlay system including an eyewear device and a server system connected via various networks.

The speaker 191 includes an electro-acoustic transducer that converts an electrical audio signal into a corresponding sound. The speaker 191 is controlled by one of the processors 422, 432 or by an audio processor 413 (FIG. 4). The speaker 191 in this example includes a series of oblong apertures, as shown, that face inward to direct the sound toward the wearer. Additional or differently oriented apertures may be implemented. In other example configurations, the eyewear device 100 is coupled to one or more speakers 191, configured to operate together (e.g., in stereo, in zones to generate surround sound) or independently, and positioned at various locations on the eyewear device 100. For example, one or more speakers 191 may be incorporated into the frame 105, temples 125, or corners 110 of the eyewear device 100.

Although shown in FIG. 2A and FIG. 2B as having two optical elements 180, the eyewear device 100 can include other arrangements, such as a single optical element (or it may not include any optical element 180), depending on the application or the intended user of the eyewear device 100. As further shown, eyewear device 100 includes a right corner 110A adjacent the right lateral side 170A of the frame 105 and a left corner 110B adjacent the left lateral side 170B of the frame 105. The corners 110 may be integrated into the frame 105 on the respective sides 170 (as illustrated) or implemented as separate components attached to the frame 105 on the respective sides 170. Alternatively, the corners 110A, 110B may be integrated into temples (not shown) attached to the frame 105.

In one example, each image display of optical assembly 180 includes an integrated image display (e.g., a first display 182A and a second display 182B). As shown in FIG. 2A, each optical assembly 180 has a display 182 that includes a suitable display matrix 177, such as a liquid crystal display (LCD), an organic light-emitting diode (OLED) display, or other such display. Each optical assembly 180 also includes an optical layer or layers 176, which can include lenses, optical coatings, prisms, mirrors, waveguides, optical strips, and other optical components in any combination. The optical layers (shown as 176A-N in FIG. 2A) can include a prism having a suitable size and configuration and including a first surface for receiving light from a display matrix and a second surface for emitting light to the eye of the user. The prism of the optical layers 176A-N extends over all or at least a portion of the respective apertures 175 formed in the left and right rims 107 to permit the user to see the second surface of the prism when the eye of the user is viewing through the corresponding rims 107. The first surface of the prism of the optical layers 176A-N faces upwardly from the frame 105 and the display matrix 177 overlies the prism so that photons and light emitted by the display matrix 177 impinge the first surface. The prism is sized and shaped so that the light is refracted within the prism and is directed toward the eye of the user by the second surface of the prism of the optical layers 176A-N. In this regard, the second surface of the prism of the optical layers 176A-N can be convex to direct the light toward the center of the eye. The prism can optionally be sized and shaped to magnify the image projected by the display matrix 177, and the light travels through the prism so that the image viewed from the second surface is larger in one or more dimensions than the image emitted from the display matrix 177.

In one example, the optical layers 176A-N may include an LCD layer that is transparent (keeping the lens open) unless and until a voltage is applied which makes the layer opaque (closing or blocking the lens). The image processor 412 on the eyewear device 100 may execute programming to apply the voltage to the LCD layer in order to produce an active shutter system, making the eyewear device 100 suitable for viewing visual content when displayed as a 3D projection. Technologies other than LCD may be used for the active shutter mode, including other types of reactive layers that are responsive to a voltage or another type of input.

In another example, the image display device of optical assembly 180 has a display 182 that includes a projection image display as shown in FIG. 2B. Each optical assembly 180 includes a respective laser projector 150, such as a three-color laser projector using a scanning mirror or galvanometer. Each laser projector 150 is disposed in or on a respective temples 125 of the eyewear device 100. Each optical assembly 180, in this example, includes one or more optical strips (shown as 155A-N in FIG. 2B), which are spaced apart and across the width of the lens of each optical assembly 180 or across a depth of the lens between the front surface and the rear surface of the lens.

As the photons projected by the laser projector 150 travel across the lens of each optical assembly 180, the photons encounter the optical strips 155A-N. When a particular photon encounters a particular optical strip, the photon is either redirected toward the user's eye, or it passes to the next optical strip. A combination of modulation of laser projector 150, and modulation of optical strips, control specific photons or beams of light. In an example, a processor controls optical strips 155A-N by initiating mechanical, acoustic, or electromagnetic signals. Although shown as having two optical assemblies 180, the eyewear device 100 can include other arrangements, such as a single or three optical assemblies, or each optical assembly 180 may have different arrangements depending on the application or intended user of the eyewear device 100.

FIG. 3 is a diagrammatic depiction of a 3D scene 306, a first raw image 302A captured using a first camera 114A, and a second raw image 302B captured using a second camera 114B. The first field of view 111A may overlap, as shown, with the second field of view 111B. The overlapping fields of view 304 represents that portion of the image captured using both cameras 114. The term 'overlapping' when referring to field of view means the matrix of pixels in the generated raw images overlap by thirty percent (30%) or more. 'Substantially overlapping' means the matrix of pixels in the generated raw images—or in the infrared image of scene—overlap by fifty percent (50%) or more. As described herein, the two raw images 302 may be processed to include a timestamp, which allows the images to be displayed together as part of a three-dimensional projection.

For the capture of stereo images, as illustrated in FIG. 3, a pair of raw red, green, and blue (RGB) images are captured of a 3D scene 306 at a given moment in time—a first raw image 302A captured using the first camera 114A and second raw image 302B captured using the second camera 114B. When the pair of raw images 302 are processed (e.g., by the image processor 412), depth images are generated. The generated depth images may be viewed on the optical assemblies 180 of an eyewear device, on another display (e.g., the image display 580 on a mobile device 401), or on a screen.

The generated depth images are in the three-dimensional space domain and can comprise a matrix of vertices on a three-dimensional location coordinate system that includes an X axis for horizontal position (e.g., length), a Y axis for vertical position (e.g., height), and a Z axis for depth (e.g., distance). Each vertex may include a color attribute (e.g., a red pixel light value, a green pixel light value, or a blue pixel light value); a position attribute (e.g., an X location coordinate, a Y location coordinate, and a Z location coordinate); a texture attribute; a reflectance attribute; or a combination thereof. The texture attribute quantifies the perceived texture of the depth image, such as the spatial arrangement of color or intensities in a region of vertices of the depth image.

FIG. 4 is a functional block diagram of an example overlay system 400 that includes an eyewear device 100, a mobile device 401, and a server system 498 connected via various networks 495 such as the Internet. As shown, the overlay system 400 includes a low-power wireless connection 425 and a high-speed wireless connection 437 between the eyewear device 100 and the mobile device 401.

The eyewear device 100 includes one or more cameras 114 that capture still images, video images, or both still and video images, as described herein. The cameras 114 may have a direct memory access (DMA) to high-speed circuitry 430 and function as a stereo camera. The cameras 114 may be used to capture initial-depth images that may be rendered into three-dimensional (3D) models that are texture-mapped images of a red, green, and blue (RGB) imaged scene. The device 100 may also include a depth sensor that uses infrared signals to estimate the position of objects relative to the device 100. The depth sensor in some examples includes one or more infrared emitter(s) and infrared camera(s) 410.

The eyewear device 100 further includes two image displays of optical assemblies 180 (one associated with the right side 170A and one associated with the left side 170B). The eyewear device 100 also includes an image display driver 442, an image processor 412, low-power circuitry 420, and high-speed circuitry 430. The image displays of optical assemblies 180 are for presenting images, including still images, video images, or still and video images. The image display driver 442 is coupled to the image displays of optical assemblies 180 in order to control the display of images.

The components shown in FIG. 4 for the eyewear device 100 are located on one or more circuit boards, for example a printed circuit board (PCB) or flexible printed circuit (FPC), located in the rims or temples. Alternatively, or additionally, the depicted components can be located in the corners, frames, hinges, or bridge of the eyewear device 100. The cameras 114 include digital camera elements such as a complementary metal-oxide-semiconductor (CMOS) image sensor, a charge-coupled device, a lens, or any other respective visible or light capturing elements that may be used to capture data, including still images or video of scenes with unknown objects.

As shown in FIG. 4, high-speed circuitry 430 includes a high-speed processor 432, a memory 434, and high-speed wireless circuitry 436. In the example, the image display driver 442 is coupled to the high-speed circuitry 430 and operated by the high-speed processor 432 in order to drive the image displays of optical assemblies 180. High-speed processor 432 may be essentially any processor capable of managing high-speed communications and operation of any general computing system. High-speed processor 432 includes processing resources needed for managing high-speed data transfers on high-speed wireless connection 437 to a wireless local area network (WLAN) using high-speed wireless circuitry 436.

In some examples, the high-speed processor 432 executes an operating system such as a LINUX operating system or other such operating system of the eyewear device 100 and the operating system is stored in memory 434 for execution. In addition to any other responsibilities, the high-speed processor 432 executes a software architecture for the eyewear device 100 that is used to manage data transfers with high-speed wireless circuitry 436. In some examples, high-speed wireless circuitry 436 is configured to implement Institute of Electrical and Electronic Engineers (IEEE) 802.11 communication standards, also referred to herein as Wi-Fi. In other examples, other high-speed communications standards may be implemented by high-speed wireless circuitry 436.

The low-power circuitry 420 includes a low-power processor 422 and low-power wireless circuitry 424. The low-power wireless circuitry 424 and the high-speed wireless circuitry 436 of the eyewear device 100 can include short-range transceivers (Bluetooth™ or Bluetooth Low-Energy (BLE)) and wireless wide, local, or wide-area network transceivers (e.g., cellular or Wi-Fi). Mobile device 401, including the transceivers communicating via the low-power wireless connection 425 and the high-speed wireless connection 437, may be implemented using details of the architecture of the eyewear device 100, as can other elements of the network 495.

Memory 434 includes any storage device capable of storing various data and applications, including, among other things, camera data generated by the cameras 114A, 114B, the infrared camera(s) 410, the image processor 412, and images generated for display by the image display driver 442 on the image display of each optical assembly 180. Although the memory 434 is shown as integrated with high-speed circuitry 430, the memory 434 in other examples may be an independent, standalone element of the eyewear device 100. In some such examples, electrical routing lines may provide a connection through a chip that includes the high-speed processor 432 from the image processor 412 or low-power processor 422 to the memory 434. In other examples, the high-speed processor 432 may manage addressing of memory 434 such that the low-power processor 422 will boot the high-speed processor 432 any time that a read or write operation involving memory 434 is to be performed.

As shown in FIG. 4, various elements of the eyewear device 100 can be coupled to the low-power circuitry 420, high-speed circuitry 430, or both. For example, the infrared camera 410 (including in some implementations an infrared emitter), the user input elements 491 (e.g., a button switch, a touchpad 181, a microphone 139), and the inertial measurement unit (IMU) 472 may be coupled to the low-power circuitry 420, high-speed circuitry 430, or both.

Figure 5:
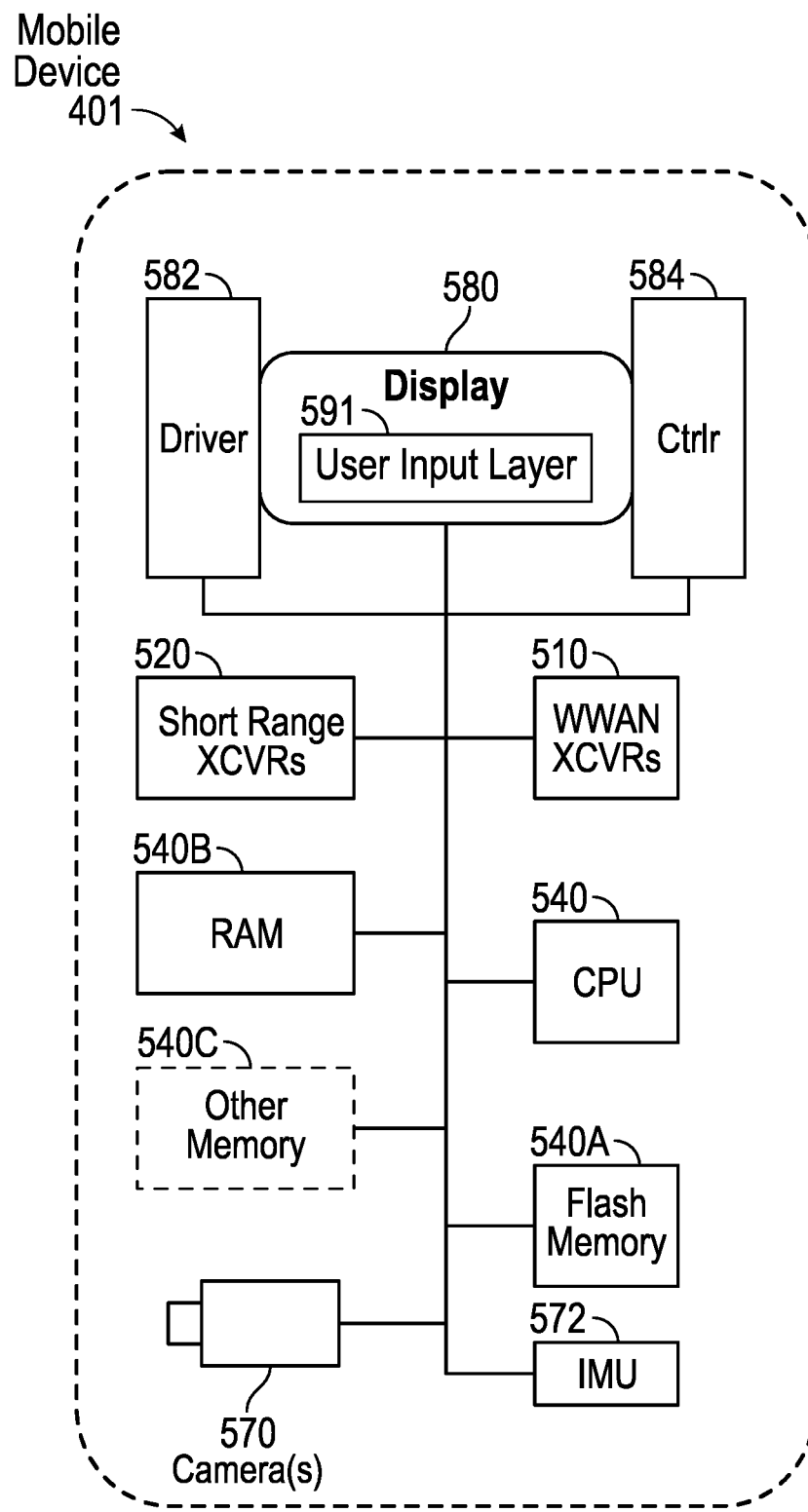
FIG. 5 is a diagrammatic representation of an example hardware configuration for a mobile device configured for use in the example overlay system of FIG. 4.

As shown in FIG. 5, which is discussed if further detail below, the CPU 540 of the mobile device 401 may be coupled to a camera system 570, a mobile display driver 582, a user input layer 591, and a memory 540A.

The server system 498 may be one or more computing devices as part of a service or network computing system, for example, that include a processor, a memory, and network communication interface to communicate over the network 495 with an eyewear device 100 and a mobile device 401.

The output components of the eyewear device 100 include visual elements, such as the image displays associated with each lens or optical assembly 180 as described with reference to FIGS. 2A and 2B (e.g., a display such as a liquid crystal display (LCD), a plasma display panel (PDP), a light emitting diode (LED) display, a projector, or a waveguide). The eyewear device 100 may include a user-facing indicator (e.g., an LED, a speaker 191, or a vibrating actuator), or an outward-facing signal (e.g., an LED, a speaker 191). The image displays of each optical assembly 180 are driven by the image display driver 442. In some example configurations, the output components of the eyewear device 100 further include additional indicators such as audible elements (e.g., speakers 191), tactile components (e.g., an actuator such as a vibratory motor to generate haptic feedback), and other signal generators. For example, the device 100 may include a user-facing set of indicators, and an outward-facing set of signals. The user-facing set of indicators are configured to be seen or otherwise sensed by the user of the device 100. For example, the device 100 may include an LED display positioned so the user can see it, one or more speakers 191 positioned to generate a sound the user can hear, or an actuator to provide haptic feedback the user can feel. The outward-facing set of signals are configured to be seen or otherwise sensed by an observer near the device 100. Similarly, the device 100 may include an LED, a speaker 191, or an actuator that is configured and positioned to be sensed by an observer.

The user input elements 491 of the eyewear device 100 may include alphanumeric input components (e.g., a touch screen or touchpad 181 configured to receive alphanumeric input, a photo-optical keyboard, or other alphanumeric-configured elements), pointer-based input components (e.g., a mouse, a touchpad 181, a trackball, a joystick, a motion sensor, or other pointing instruments), tactile input components (e.g., a button switch, a touch screen or touchpad 181 that senses the location, force or location and force of touches or touch gestures, or other tactile-configured elements), and audio input components (e.g., a microphone 139), and the like. The mobile device 401 and the server system 498 may include alphanumeric, pointer-based, tactile, audio, and other input components.

In some examples, the eyewear device 100 includes a collection of motion-sensing components referred to as an IMU 472. The motion-sensing components may be micro-electro-mechanical systems (MEMS) with microscopic moving parts, often small enough to be part of a microchip. The IMU 472 in some example configurations includes an accelerometer, a gyroscope, and a magnetometer. The accelerometer senses the linear acceleration of the device 100 (including the acceleration due to gravity) relative to three orthogonal axes (x, y, z). The gyroscope senses the angular velocity of the device 100 about three axes of rotation (pitch, roll, yaw). Together, the accelerometer and gyroscope can provide position, orientation, and motion data about the device relative to six axes (x, y, z, pitch, roll, yaw). The magnetometer, if present, senses the heading of the device 100 relative to magnetic north. The position of the device 100 may be determined by location sensors, such as a GPS unit 473, one or more transceivers to generate relative position coordinates, altitude sensors or barometers, and other orientation sensors. Such positioning system coordinates can also be received over the wireless connections 425, 437 from the mobile device 401 via the low-power wireless circuitry 424 or the high-speed wireless circuitry 436.

The IMU 472 may include or cooperate with a digital motion processor or programming that gathers the raw data from the components and compute a number of useful values about the position, orientation, and motion of the device 100. For example, the acceleration data gathered from the accelerometer can be integrated to obtain the velocity relative to each axis (x, y, z); and integrated again to obtain the position of the device 100 (in linear coordinates, x, y, and z). The angular velocity data from the gyroscope can be integrated to obtain the position of the device 100 (in spherical coordinates). The programming for computing these useful values may be stored in memory 434 and executed by the high-speed processor 432 of the eyewear device 100.

The eyewear device 100 may optionally include additional peripheral sensors, such as biometric sensors, specialty sensors, or display elements integrated with eyewear device 100. For example, peripheral device elements may include any I/O components including output components, motion components, position components, or any other such elements described herein. For example, the biometric sensors may include components to detect expressions (e.g., hand expressions, facial expressions, vocal expressions, body gestures, or eye tracking), to measure bio signals (e.g., blood pressure, heart rate, body temperature, perspiration, or brain waves), or to identify a person (e.g., identification based on voice, retina, facial characteristics, fingerprints, or electrical bio signals such as electroencephalogram data), and the like.

The mobile device 401 may be a smartphone, tablet, laptop computer, access point, or any other such device capable of connecting with eyewear device 100 using both a low-power wireless connection 425 and a high-speed wireless connection 437. Mobile device 401 is connected to server system 498 and network 495. The network 495 may include any combination of wired and wireless connections.

The overlay system 400, as shown in FIG. 4, includes a computing device, such as mobile device 401, coupled to an eyewear device 100 over a network 495. The overlay system 400 includes a memory (e.g., a non-transitory computer readable media) for storing instructions and a processor for executing the instructions. In some implementations, the memory and processing functions of the overlay system 400 can be shared or distributed across the processors and memories of the eyewear device 100, the mobile device 401, and/or the server system 498.

In some implementations, the overlay system 400 includes one or more elements or modules, referred to herein as an overlay application 910, an image registration tool 912, a localization system 915, an image processing system 920, and a voice recognition module 925.

The overlay application 910 in some implementations renders and presents a medical image overlay 800 on the display 182, as described herein.

The image registration tool 912 in some implementations includes any of a variety of image registration or image alignment algorithms for transforming one or more sets of data (e.g., medical image data) into a single or common coordinate system. The field of image registration applies a variety of transformation models, including linear models, vector space models, elastic or non-rigid models, quadratics, parameterized, diffeomorphic mapping, vector space models, and other mathematical and computational models. In the context of medical imaging, the image registration tool 912 in some implementations transforms the location, orientation, and size of a medical image 810 of a target 50 according to a single coordinate system (e.g., a physical coordinate system 610 associated with a physical environment 600) such that, when presented on a display the registered medical image appears at a location, in an orientation, and at a size that corresponds with the location, orientation, and size of the target 50.

The localization system 915 in some implementations obtains localization data for use in determining the position of the eyewear device 100 relative to a physical environment 600. For example, the localization system 915 may access the frames of video data 900 captured using the camera 114B to determine the eyewear device location 840 in three-dimensional coordinates relative to the physical environment (with or without reference to data from other sources, such as an inertial measurement unit or IMU 472). As used herein, the term 'frames of video data' refers to the video motion data captured using the one or more cameras 114A, 114B coupled to the eyewear device 100, including images, spatial data, and related information captured using essentially any sensor component of a camera in any form and at any sample rate. In some implementations, the localization data may be derived from the frames of motion data captured using the IMU 472, from data gathered by a GPS unit 473, or from a combination thereof.

The image processing system 920 in some implementations presents a medical image overlay 800, as described herein, on a display 182 of a respective optical assembly 180, in cooperation with the image display driver 442 and the image processor 412. The medical image overlay 800 in some implementations includes one or more medical images 810 that have been registered to the physical environment 600 using the image registration tool 912.

The voice recognition module 925 in some implementations receives human speech, converts the received speech into frames of audio data, identifies an inquiry or a request based on the audio data, and executes an action that is correlated with and responsive to the identified inquiry or request.

FIG. 5 is a high-level functional block diagram of an example mobile device 401. Mobile device 401 includes a flash memory 540A which stores programming to be executed by the CPU 540 to perform all or a subset of the functions described herein.

The mobile device 401 may include a camera 570 that comprises at least two cameras (e.g., first and second visible-light cameras with overlapping fields of view) or at least one camera and a depth sensor with substantially overlapping fields of view. Flash memory 540A may further include multiple images or video, which are generated via the camera 570.

As shown, the mobile device 401 includes an image display 580, a mobile display driver 582 to control the image display 580, and a display controller 584. In the example of FIG. 5, the image display 580 includes a user input layer 591 (e.g., a touchscreen) that is layered on top of or otherwise integrated into the screen used by the image display 580.

Examples of touchscreen-type mobile devices that may be used include (but are not limited to) a smart phone, a personal digital assistant (PDA), a tablet computer, a laptop computer, or other portable device. However, the structure and operation of the touchscreen-type devices is provided by way of example; the subject technology as described herein is not intended to be limited thereto. For purposes of this discussion, FIG. 5 therefore provides a block diagram illustration of the example mobile device 401 with a user interface that includes a touchscreen input layer 591 for receiving input (by touch, multi-touch, or gesture, and the like, by hand, stylus, or other tool) and an image display 580 for displaying content.

As shown in FIG. 5, the mobile device 401 includes at least one digital transceiver (XCVR) 510, shown as WWAN XCVRs, for digital wireless communications via a wide-area wireless mobile communication network. The mobile device 401 also includes additional digital or analog transceivers, such as short-range transceivers (XCVRs) 520 for short-range network communication, such as via NFC, VLC, DECT, ZigBee, Bluetooth™, or Wi-Fi. For example, short range XCVRs 520 may take the form of any available two-way wireless local area network (WLAN) transceiver of a type that is compatible with one or more standard protocols of communication implemented in wireless local area networks, such as one of the Wi-Fi standards under IEEE 802.11.

To generate location coordinates for positioning of the mobile device 401, the mobile device 401 can include a global positioning system (GPS) receiver. Alternatively, or additionally the mobile device 401 can utilize either or both the short range XCVRs 520 and WWAN XCVRs 510 for generating location coordinates for positioning. For example, cellular network, Wi-Fi, or Bluetooth™ based positioning systems can generate accurate location coordinates, particularly when used in combination. Such location coordinates can be transmitted to the eyewear device over one or more network connections via XCVRs 510, 520.

The mobile device 401 in some examples includes a collection of motion-sensing components referred to as an inertial measurement unit (IMU) 572 for sensing the position, orientation, and motion of the mobile device 401. The motion-sensing components may be micro-electro-mechanical systems (MEMS) with microscopic moving parts, often small enough to be part of a microchip. The inertial measurement unit (IMU) 572 in some example configurations includes an accelerometer, a gyroscope, and a magnetometer. The accelerometer senses the linear acceleration of the mobile device 401 (including the acceleration due to gravity) relative to three orthogonal axes (x, y, z). The gyroscope senses the angular velocity of the mobile device 401 about three axes of rotation (pitch, roll, yaw). Together, the accelerometer and gyroscope can provide position, orientation, and motion data about the device relative to six axes (x, y, z, pitch, roll, yaw). The magnetometer, if present, senses the heading of the mobile device 401 relative to magnetic north.

The IMU 572 may include or cooperate with a digital motion processor or programming that gathers the raw data from the components and compute a number of useful values about the position, orientation, and motion of the mobile device 401. For example, the acceleration data gathered from the accelerometer can be integrated to obtain the velocity relative to each axis (x, y, z); and integrated again to obtain the position of the mobile device 401 (in linear coordinates, x, y, and z). The angular velocity data from the gyroscope can be integrated to obtain the position of the mobile device 401 (in spherical coordinates). The programming for computing these useful values may be stored in on or more memory elements 540A, 540B, 540C and executed by the CPU 540 of the mobile device 401.

The transceivers 510, 520 (i.e., the network communication interface) conforms to one or more of the various digital wireless communication standards utilized by modern mobile networks. Examples of WWAN transceivers 510 include (but are not limited to) transceivers configured to operate in accordance with Code Division Multiple Access (CDMA) and 3rd Generation Partnership Project (3GPP) network technologies including, for example and without limitation, 3GPP type 2 (or 3GPP2) and LTE, at times referred to as "4G." For example, the transceivers 510, 520 provide two-way wireless communication of information including digitized audio signals, still image and video signals, web page information for display as well as web-related inputs, and various types of mobile message communications to/from the mobile device 401.

The mobile device 401 further includes a microprocessor that functions as a central processing unit (CPU); shown as CPU 540 in FIG. 4. A processor is a circuit having elements structured and arranged to perform one or more processing functions, typically various data processing functions. Although discrete logic components could be used, the examples utilize components forming a programmable CPU. A microprocessor for example includes one or more integrated circuit (IC) chips incorporating the electronic elements to perform the functions of the CPU. The CPU 540, for example, may be based on any known or available microprocessor architecture, such as a Reduced Instruction Set Computing (RISC) using an ARM architecture, as commonly used today in mobile devices and other portable electronic devices. Of course, other arrangements of processor circuitry may be used to form the CPU 540 or processor hardware in smartphone, laptop computer, and tablet.

The CPU 540 serves as a programmable host controller for the mobile device 401 by configuring the mobile device 401 to perform various operations, for example, in accordance with instructions or programming executable by CPU 540. For example, such operations may include various general operations of the mobile device, as well as operations related to the programming for applications on the mobile device. Although a processor may be configured by use of hardwired logic, typical processors in mobile devices are general processing circuits configured by execution of programming.

The mobile device 401 includes a memory or storage system, for storing programming and data. In the example, the memory system may include a flash memory 540A, a random-access memory (RAM) 540B, and other memory components 540C, as needed. The RAM 540B serves as short-term storage for instructions and data being handled by the CPU 540, e.g., as a working data processing memory. The flash memory 540A typically provides longer-term storage.

Hence, in the example of mobile device 401, the flash memory 540A is used to store programming or instructions for execution by the CPU 540. Depending on the type of device, the mobile device 401 stores and runs a mobile operating system through which specific applications are executed. Examples of mobile operating systems include Google Android, Apple iOS (for iPhone or iPad devices), Windows Mobile, Amazon Fire OS, RIM BlackBerry OS, or the like.

The processor 432 within the eyewear device 100 may construct a map of the environment surrounding the eyewear device 100, determine a location of the eyewear device within the map of the environment, and determine a relative position of the eyewear device to one or more objects in the mapped environment. The processor 432 may construct the map and determine location and position information using a simultaneous localization and mapping (SLAM) algorithm applied to data received from one or more sensors. Sensor data includes images received from one or both of the cameras 114A, 114B, distance(s) received from a laser range finder, position information received from a GPS unit 473, motion and acceleration data received from an IMU 572, or a combination of data from such sensors, or from other sensors that provide data useful in determining positional information. In the context of augmented reality, a SLAM algorithm is used to construct and update a map of an environment, while simultaneously tracking and updating the location of a device (or a user) within the mapped environment. The mathematical solution can be approximated using various statistical methods, such as particle filters, Kalman filters, extended Kalman filters, and covariance intersection. In a system that includes a high-definition (HD) video camera that captures video at a high frame rate (e.g., thirty frames per second), the SLAM algorithm updates the map and the location of objects at least as frequently as the frame rate; in other words, calculating and updating the mapping and localization thirty times per second.

Sensor data includes image(s) received from one or both cameras 114A, 114B, distance(s) received from a laser range finder, position information received from a GPS unit 473, motion and acceleration data received from an IMU 472, or a combination of data from such sensors, or from other sensors that provide data useful in determining positional information.

Figure 6:
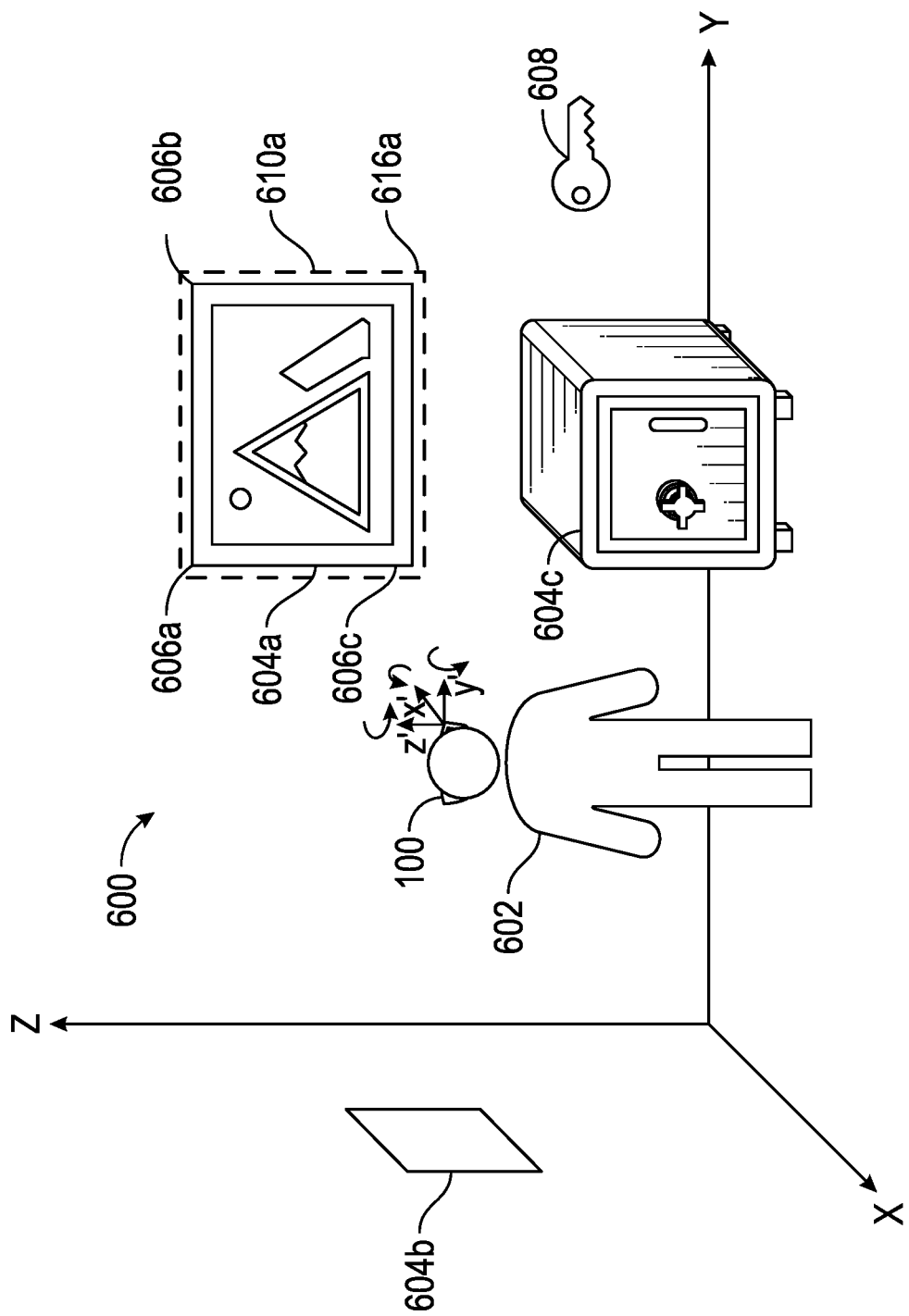
FIG. 6 is a perspective view of a user in an example environment for use in describing simultaneous localization and mapping (SLAM)

FIG. 6 depicts an example physical environment 600 along with elements that are useful when using a SLAM algorithm and other types of tracking applications (e.g., natural feature tracking (NFT), hand tracking, etc.). A user 602 of eyewear device 100 is present in an example physical environment 600 (which, in FIG. 6, is an interior room). The processor 432 of the eyewear device 100 determines the position of the eyewear device 100 with respect to one or more physical objects 604 within the environment 600 using captured image data, constructs a map of the environment 600 using a coordinate system (e.g., a Cartesian coordinate system (x, y, z)) for the environment 600, and determines the position relative to the coordinate system. Additionally, the processor 432 determines a head pose (roll, pitch, and yaw) of the eyewear device 100 within the environment by using two or more location points (e.g., three location points 606a, 606b, and 606c) associated with a single object 604a, or by using one or more location points 606 associated with two or more objects 604a, 604b, 604c. The processor 432 of the eyewear device 100 may position a virtual object 608 (such as the key shown in FIG. 6) within the environment 600 for viewing during an augmented reality experience.

The localization system 915 in some examples includes a virtual marker 610a associated with a virtual object 608 in the physical environment 600. In an augmented reality environment, in some implementations, markers are registered at locations in the physical environment 600 to assist electronic devices with the task of tracking and updating the location of users, devices, and objects (virtual and physical) relative to the physical environment. Markers are sometimes registered to a high-contrast physical object, such as the relatively dark object, such as the framed picture 604a, mounted on a lighter-colored wall, to assist cameras and other sensors with the task of detecting the marker. The markers may be assigned and registered in a memory by the eyewear device 100 operating within the environment. In some implementations, the markers are assigned and registered in the memory of other devices in the network.

The localization system 915 tracks physical objects and virtual objects within the physical environment 600 relative to the eyewear device 100. For a physical object 604 (e.g., safe 604c) the localization system 915 continuously analyzes captured images of the physical environment 600 to identify the object 604 and to determine its location relative to the eyewear device 100 (e.g., by applying a SLAM algorithm). The localization system 915 maintains and updates the determined location information for the physical object 604 in memory, thereby tracking the physical object 604 as the eyewear device 100 moves through the physical environment 600. For a virtual object 608 (e.g., key) the localization system 915 establishes or designates an initial location for the virtual object 608 corresponding to a location or a physical object 604 in the environment 600 (or, in some implementations, at a location relative to the eyewear device 100). The localization system 915 maintains and updates the virtual object 608 location information, for example, in accordance with a movement algorithm associated with the virtual object 608, in response to movement of the eyewear device 100 through the environment, or a combination thereof, thereby tracking the virtual object 608 as the eyewear device 100 moves through the environment.

Markers can be encoded with or otherwise linked to information. A marker might include position information, a physical code (such as a bar code or a QR code; either visible to the user or hidden), or a combination thereof. A set of data associated with the marker is stored in the memory 434 of the eyewear device 100. The set of data includes information about the marker 610a, the marker's position (location and orientation), one or more virtual objects, or a combination thereof. The marker position may include three-dimensional coordinates for one or more marker landmarks 616a, such as the corner of the generally rectangular marker 610a shown in FIG. 6. The marker location may be expressed relative to real-world geographic coordinates, a system of marker coordinates, a position of the eyewear device 100, or other coordinate system. The one or more virtual objects associated with the marker 610a may include any of a variety of materials, including still images, video, audio, tactile feedback, executable applications, interactive user interfaces and experiences, and combinations or sequences of such material. Any type of content capable of being stored in a memory and retrieved when the marker 610a is encountered or associated with an assigned marker may be classified as a virtual object in this context. The virtual key 608 shown in FIG. 6, for example, is a virtual object displayed as a still image, either 2D or 3D, at a marker location.

In one example, the marker 610a may be registered in memory as being located near and associated with a physical object 604a (e.g., the framed work of art shown in FIG. 6). In another example, the marker may be registered in memory as being a particular position with respect to the eyewear device 100.

Figure 7:
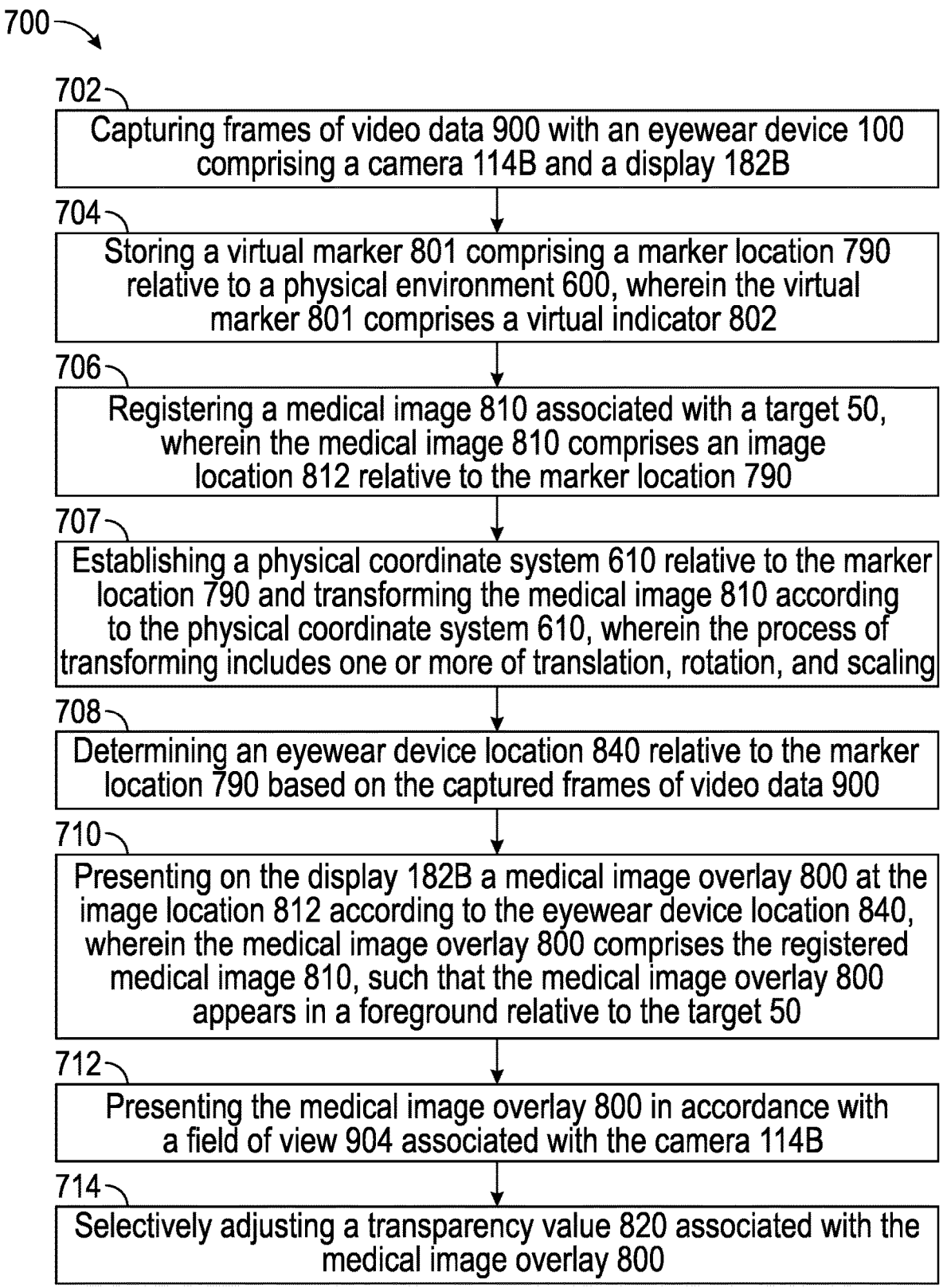
FIG. 7 is a flow chart listing the steps in an example method of presenting a medical image overlay on a display.

FIG. 7 is a flow chart 700 of an example method of presenting a medical image overlay 800 on the display 182B of an eyewear device 100. Although the steps are described with reference to the eyewear device 100 described herein, other implementations of the steps described, for other types of devices, will be understood by one of skill in the art from the description herein. One or more of the steps shown and described may be performed simultaneously, in a series, in an order other than shown and described, or in conjunction with additional steps. Some steps may be omitted or, in some applications, repeated.

The overlay application 910 described herein, in some implementations, launches in response to receiving a selection through a user interface (e.g., selecting from a menu, pressing a button, using a touchpad) or through some other input means (e.g., a hand gesture detected in captured images, a finger touch 681 on the touchpad 181, a voice command).

Block 702 in FIG. 7 recites an example step of capturing frames of video data 900 with the camera 114A, 114B of an eyewear device 100. In some implementations, the process of capturing frames of video data 900 is ongoing during active use of the eyewear device 100. In other examples, the process of capturing starts in response to receiving a selection through a user interface or through some other input means. The example method step, at block 702, in some implementations, includes storing the captured frames of video data 900 in memory 434 on the eyewear device 100, at least temporarily, such that the frames of video data 900 are available for uses including processing and analysis.

Block 704 in FIG. 7 recites an example step of storing a virtual marker 801 associated with a target of interest (e.g., a bone or a tooth) in a physical environment 600. The process of storing a virtual marker 801, in some implementations, includes a processor of the eyewear device 100 associating the virtual marker 801 with a marker location 790 in the physical environment 600 (as opposed to a position on a display 182B). In this aspect, the virtual marker location 790 is defined relative to the physical environment (e.g., relative to a physical coordinate system 610, as shown in FIG. 8C). The marker location 790 in this example is fixed relative to the surrounding physical environment 600, without regard to the display 182B or the motion of the eyewear device 100 through the physical environment 600.

FIG. 8C is a perspective illustration of two example virtual markers 801A, 801B as seen through a display 182B.

The virtual marker 801A, 801B in some implementations comprises a marker location 790A, 790B, and a virtual indicator 802A, 802B presented near the virtual marker 801A, 801B. The virtual indicator 802A, 802B in some implementations included a highlight (e.g., a circular mark as shown in FIG. 8C) or indicia (e.g., visible, audible, or tactile) which is selectively presented on the display 182B to facilitate identification of a virtual marker 801A, 801B. In some implementations the virtual indicator 802A, 802B includes a default element or shape which can be selected or changed through a user interface. The marker location 790A, 790B in some implementations, as shown in FIG. 8C, is located near but not necessarily centered on the virtual marker 801A, 801B. In some implementations, the virtual marker 801A, 801B does not include a virtual indicator 802A, 80B or any other type of indicator.

In some implementations, the process of storing the virtual marker 801 includes presenting a virtual indicator 802 on the display 182B (e.g., at or near the center of the display 182B) as a visual guide. In this example, the user can place the virtual indicator 802 on or near any trial location for the marker location 790 (e.g., near a particular tooth). Then, in this example storing process, the overlay application 910 receives an input (e.g., a finger tap 681 on the touchpad 181, a voice command, or a gesture) indicating where to place and store the virtual marker 801. In other implementations, the process of storing the virtual marker 801 includes receiving a voice command or other input indicating a particular location (e.g., tooth number 14, occlusal surface) relative to a physical environment 600 (e.g., a patient's mouth) which has been mapped and stored in memory. The process of storing the virtual marker 801 in some implementations includes using the touchpad 181 to control the position of a cursor (not shown) presented on then display 182B so that the user can place the cursor at a current location (e.g., near a particular tooth) and execute a selection action and store the virtual marker 801 at the current location.

The eyewear device 100 in some implementations includes a voice recognition module 925, as described herein, and a microphone 139 coupled to a speaker 191. The voice recognition module 925 in some implementations configures the processor 432 to perceive human speech, convert the received speech into frames of audio data, identify a first inquiry based on converted frames of audio data, and then perform an action in response to and in accordance with the identified first inquiry. For example, the human speech may include a verbal command (e.g., "set marker location") and, in response, the identified first inquiry causes the overlay application 910 to execute a selection action and store the virtual marker 801 at the current location.

The process of storing the virtual marker 801 in some implementations includes, after a selection has been input, presenting a virtual indicator 802 on the display 182B. If the selected marker location 790 (as indicated by the virtual indicator 802) is acceptable, the user may accept the location 790; if not, the user may cancel and select again.

Block 706 recites an example step of registering a medical image 810 associated with a target 50, wherein the medical image 810 comprises an image location 812 relative to the marker location 790.

As used herein, the term 'medical image' refers to and includes the information or data gathered by any of a variety of imaging technology, whether applied in the medical context or not, including but not limited to radiography (X-ray), computed tomography (CT), magnetic resonance imaging (MM), ultrasound, endoscopy, elastography, tactile imaging, thermography, functional imaging, positron emission tomography (PET), single-photon emission computed tomography (SPECT), and various types of photography.

As used herein, the term 'target' refers to and includes an item such as an object, a material, a substance, a structure, a tissue, or a cell, and any part or piece of such an item. A target may be biological in nature (e.g., human or animal tissue, such as bones or teeth). The term 'target of interest' refers to and includes the target and may include an area, region, or volume of space near or surrounding the target.

Although the overlay system 400 and overlay application 910 are described herein in the context of medical images and biological targets, the technology described may be applied to essentially any type of activity or work in which an image overlay is a useful or desired tool.

Figure 8A:
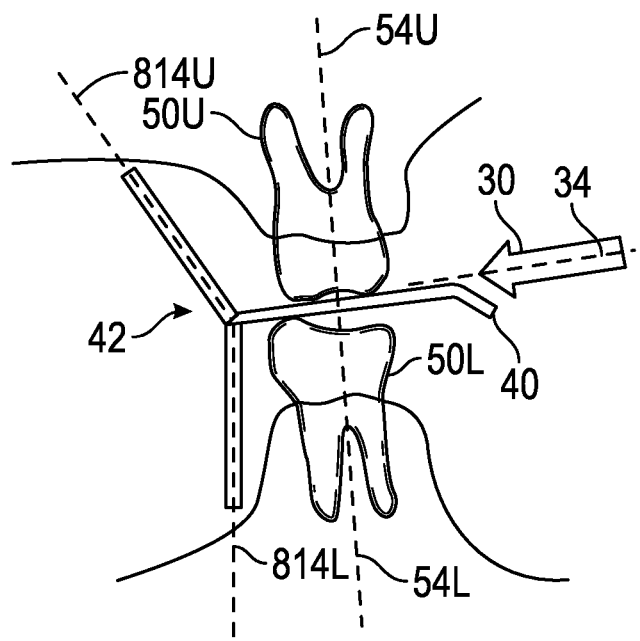
FIG. 8A is an illustration of a medical film relative to target of interest in an example process of capturing an example medical image.
Figure 8B:
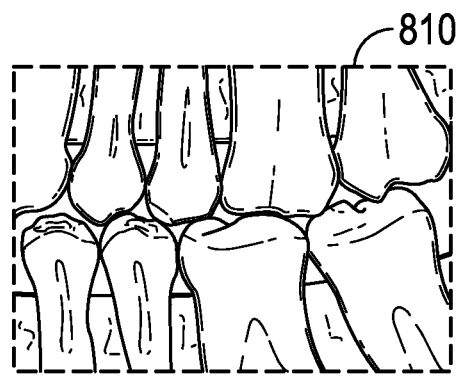
FIG. 8B is an illustration of example medical images.
Figure 8B:
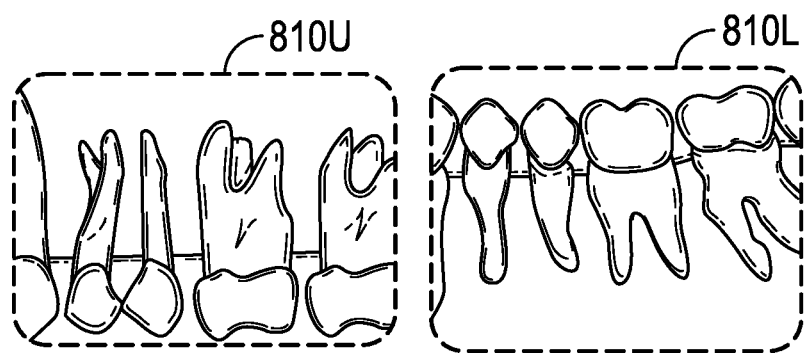
Figure 8C:
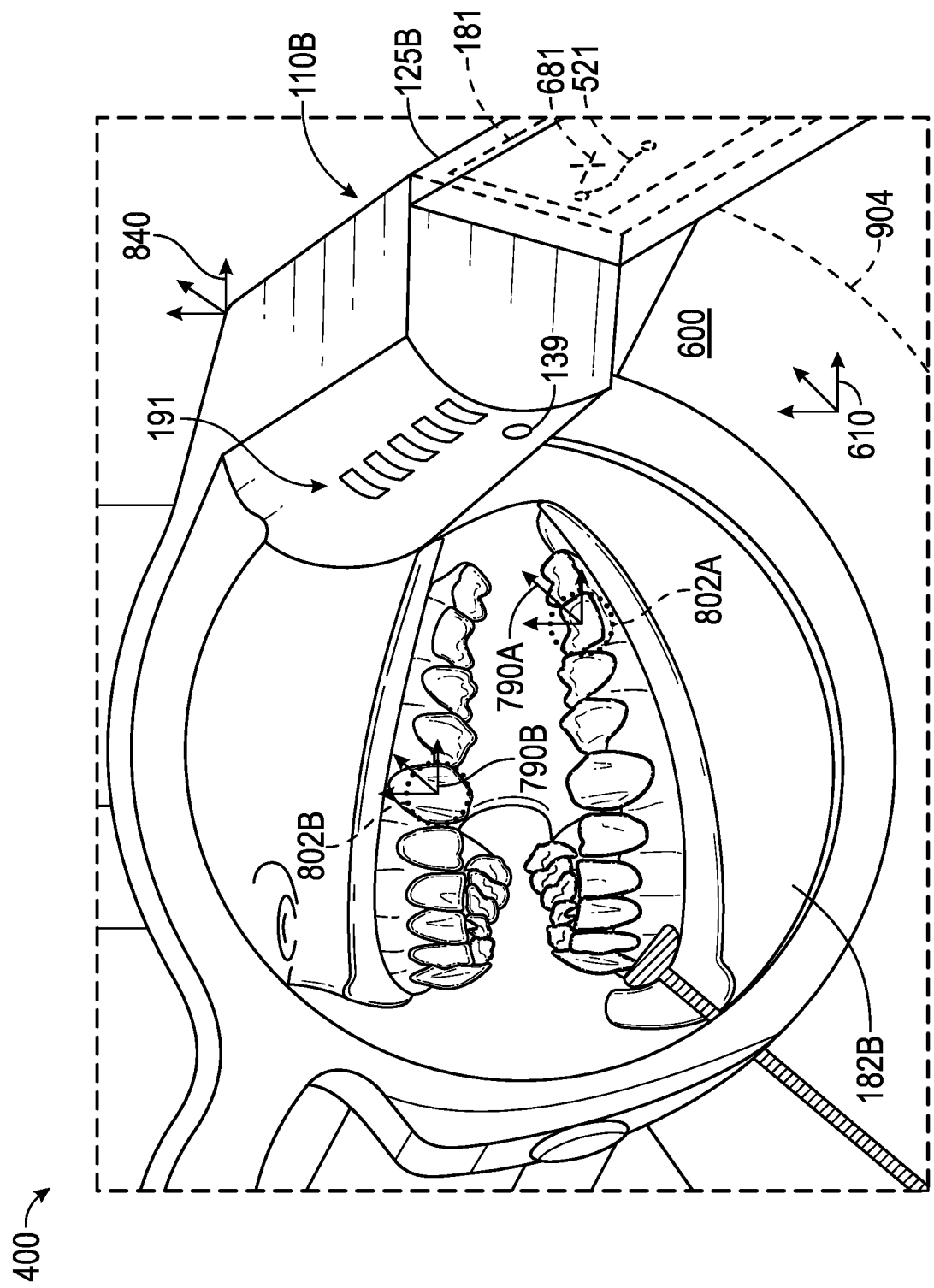
FIG. 8C is a perspective view of example virtual markers relative to a physical environment, as presented on an example display.

FIG. 8A is an illustration of a medical film 42 relative to target of interest (e.g., an upper tooth 50U and a lower tooth 50L) in an example process of capturing one or more medical images 810 (shown in FIG. 8B). The upper tooth 50U is characterized by an upper tooth axis 54U. The lower tooth 50L is characterized by a lower tooth axis 54L. In this example, the medical film 42 is a bitewing film that includes a film holder 40 placed between the teeth 50U, 50L. The bitewing film 42 includes an upper film portion extending along an upper film axis 814U and a lower film portion extending along a lower film axis 814L. The x-ray beam 30 is directed along a beam direction 34 toward the film 42.

FIG. 8B includes an illustration of an example bitewing image 810, an upper periapical image 810U, and a lower periapical image 810L. As shown, the periapical images 810U, 810L include in some implementations the full length of the teeth, from crown to root.

Referring again to block 706, the medical image 810 in some implementations comprises an image location 812 relative to the marker location 790. For example, as shown in FIG. 8C, one of the example virtual markers 801A is associated with a marker location 790A which is defined (e.g., in three dimensions) relative to the physical environment 600. The image location 812 includes three-dimensional coordinates and, in some implementations, a vector associated with the medical image 810. In this example, the vector may define a plane (e.g., ten degrees, relative to the marker location 790) and a distance (e.g., forty millimeters in length), such that the orientation and the size of the medical image 810 is part of the stored image location 812.

Figure 8D:
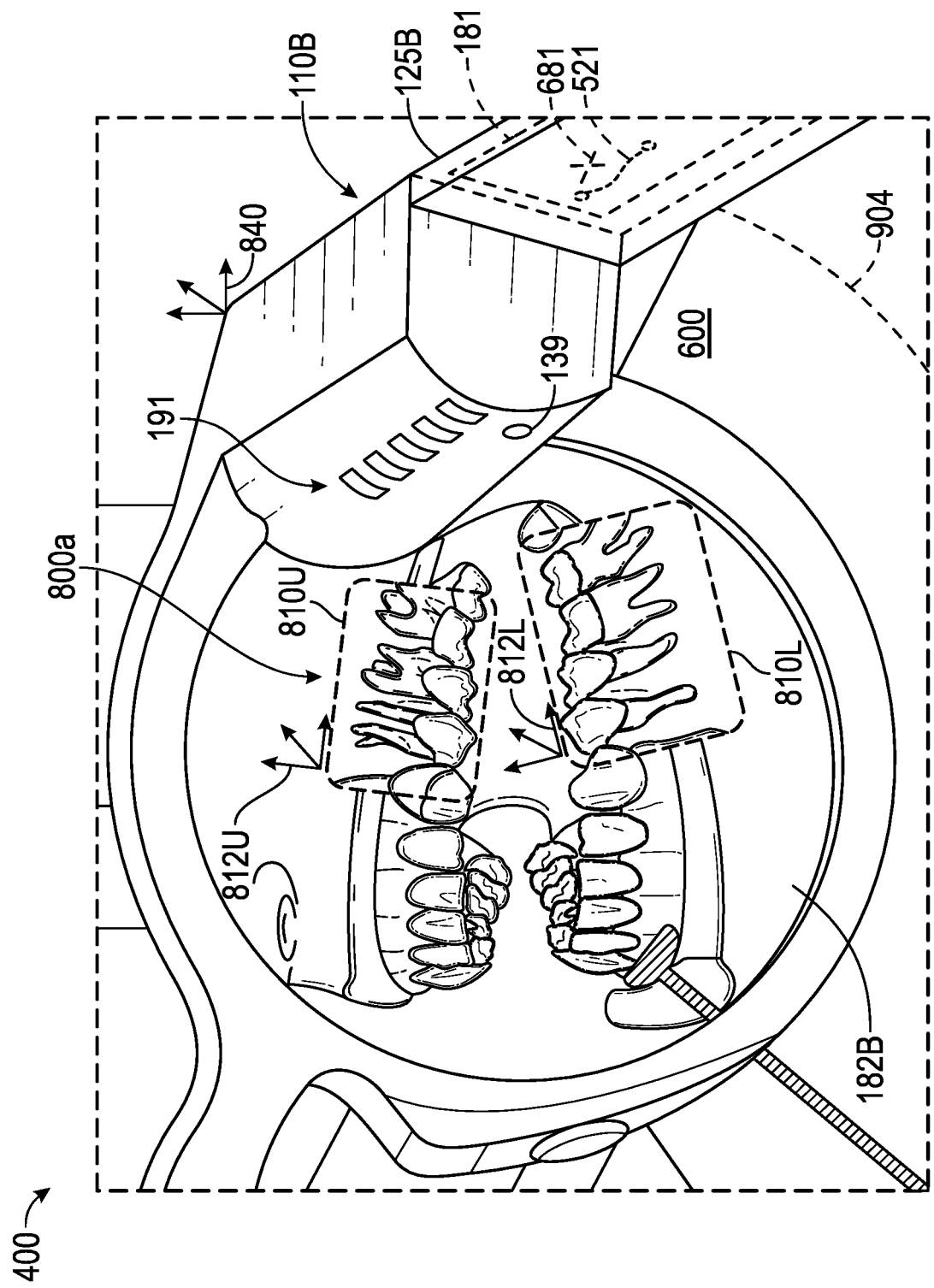
FIG. 8D is a perspective view of an example medical image overlay comprising one or medical images presented on a display as an overlay in the foreground relative to the target of interest.

The marker location 790A shown in FIG. 8C is located near a bottom tooth. In some implementations, the medical image location 812 is defined relative to the marker location 790. For example, as shown in FIG. 8D, the lower medical image 810L comprises a lower image location 812L, which is defined relative to one or more marker locations 790A, 790B (shown in FIG. 8C). In this aspect, the image locations 812U, 812L are defined relative to or otherwise permanently associated with one or more marker locations 790A, 790B in the physical environment 600.

The example step of registering a medical image 810 at block 706 in some implementations includes applying or otherwise using an image registration tool 912 as described herein. The process of image registration includes transforming one or more sets of data (e.g., medical image data) having its own coordinates (e.g., location, orientation, size) into another coordinate system (e.g., a physical coordinate system 610 associated with a physical environment 600). The image registration tool 912 in some implementations applies a linear transformation model and vector mathematics to transform the location, orientation, and size of a medical image 810 so that its location, orientation, and size appears to be relatively accurate when the medical image 810 is presented (e.g., on a display 182) relative to a physical environment 600.

The process of registering a medical image 810 in some implementations includes establishing the image location 812 relative to the target 50 (e.g., relative to the marker location 790 nearest the target 50) such that the medical image 810, when registered, will be presented as an overlay in the foreground relative to the target 50. Referring again to FIG. 8A, for example, the medical film 42 is located behind the target 50 (e.g., in the background relative to the upper tooth 50U). If the upper image location 812U were established at or near the location of the medical film 42 (e.g., behind the tooth 50U) then the resulting medical image 810U would be presented in the background (e.g., behind the upper tooth 50U) where the medical image 810U would not be viewable. Therefore, in order to present the medical image overlay 800 (e.g., medical image 810u) in the foreground, the process of registering a medical image 810U in some implementations (e.g., using the image registration tool 912) includes establishing the image location 812U in the foreground relative to the target 50 (e.g., in front of the upper tooth 50U).

Block 707 recites an example step of registering a medical image 810 by transforming the medical image 810 according to a physical coordinate system 610. The step at block 707 includes establishing a physical coordinate system 610 relative to the marker location 790, as shown in FIG. 8C. The process of transforming the medical image 810 in some implementations includes translation, rotation, and scaling. For example, applying a linear transformation model generally involves adjusting the translation (e.g., the location of the medical image 810 as defined by coordinates in two or three dimensions), the rotation (e.g., the angle of the medical image 810), and scaling (e.g., the size of the medical image 810) relative to the physical coordinate system 610.

Block 708 recites an example step of estimating the eyewear device location 840 relative to the marker location 790 (e.g., where the virtual marker 801 and the selected tooth is located). After the marker registering process, as the eyewear device 100 moves through the physical environment 600 its location changes relative to the marker location 790. The current electronic eyewear device location 840 in some implementations is estimated using the localization system 915 as described herein.

The localization system 915 on the eyewear device 100 in some implementations configures the processor 432 of the eyewear device 100 to obtain localization data based on the captured frames of video data 900 from the camera 114A, 114B, and in some implementations based on the motion data gathered by the IMU 472. In some implementations, the localization system 915 constructs a virtual map of one or more objects within the camera field of view 904 using a SLAM algorithm, as described herein, updating the map and the location of objects at least as frequently as the camera 114A, 114B captures video data 900. Frequent analysis of high-frequency video data 900 facilitates the detection of relatively subtle motions of the eyewear device 100 over time.

The step of estimating the electronic eyewear device location 840 relative to the marker location 790 in some implementations includes calculating a correlation between the marker location 790 and the current electronic eyewear device location 840. The term correlation refers to and includes one or more vectors, matrices, formulas, or other mathematical expressions sufficient to define the three-dimensional distance between the marker location 790 and the current electronic eyewear device location 840. The current electronic eyewear device location 840 is associated with the three-dimensional position and orientation (e.g., head pose, gaze direction) of the display 182 because the display 182 is supported by the frame of the eyewear device 100. In this aspect, the process of correlation performs the function of calibrating the motion of the eyewear device 100 with the marker location 790. Because the localization process occurs frequently, the process of correlation between the eyewear device location 840 and the marker location 790 produces accurate and near real-time tracking of the current electronic eyewear device location 840 relative to the marker location 790.

In some implementations, the process of estimating the current electronic eyewear device location 840 is based on the frames of motion data captured using the IMU 472, or on the frames of video data 900 captured using a camera 114A coupled to the eyewear device 100, or a combination of both. The process of estimating the current electronic eyewear device location 840 in some implementations is executed about as frequently as the IMU 472 captures motion data (e.g., one hundred times per second, based on an IMU sample rate of 100 Hz (samples per second)). In some implementations, the process of estimating the current electronic eyewear device location 840 occurs at a predefined and configurable frequency, and the IMU 472 is configured to captured frames of motion data at a compatible rate.

Block 710 in FIG. 7 recites an example step of presenting on the display 182B a medical image overlay 800 at the image location 812 according to the current electronic eyewear device location 840. The medical image overlay 800 is presented at the image location 812, which is associated with the medical image 810. In some implementations the medical image overlay 800 comprises one or more medical images 810, as registered (e.g., as described at block 706). In some implementations the medical image overlay 800 comprises a part, portion, or segment of one or more medical images 810, as registered.

As shown in FIG. 8D, the medical image overlay 800a in this example includes a lower medical image 810L presented at image location 812L and an upper medical image 810U presented at image location 812U. The medical images 810L, 810U have been registered with the physical environment 600, as described herein. As shown in FIG. 8D, a number of real objects in the physical environment 600 (e.g., the mouth and other teeth) are viewable through the semi-transparent lens assembly and display 182B. The process of registering and presenting produces a medical image overlay 800a that closely matches the location, orientation, and size of the real objects. For example, as shown in FIG. 8D, the medical image 810L closely matches the location, orientation, and size of the real objects (e.g., the four real, lower teeth which were the subject of the medical image 810L). In this aspect, the medical image overlay 800a provides an accurate view of the normally-unseen features of the target (e.g., the dentin, pulp chamber, alveolar bone, and roots of the four subject lower teeth) by presenting the medical image 810L at the proper location and scale.

The process of presenting a medical image overlay 800 in some implementations includes presenting the medical images 810L, 810U as an overlay relative to the physical environment 600, such that the medical image overlay 800 is persistently viewable in the foreground relative to the real objects in the physical environment. For example, as shown in FIG. 8D, the medical image overlay 800a is presented as an overlay (e.g., in the foreground) relative to the physical environment 600 (e.g., in front of the teeth), such that the medical image overlay 800 is persistently viewable relative to other objects in the physical environment 600.

Figure 8E:
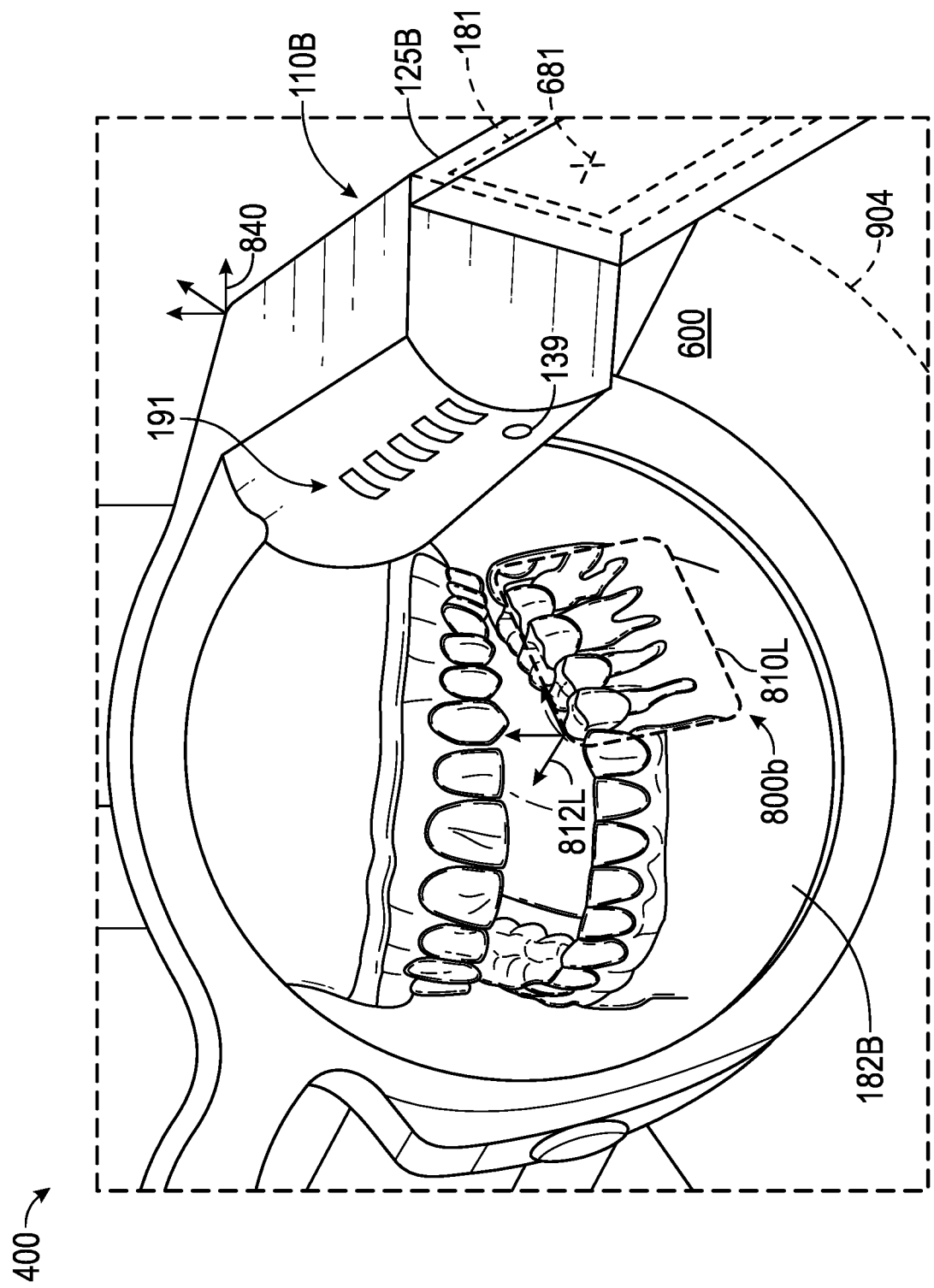
FIG. 8E is a perspective view of another example medical image overlay presented on a display.

FIG. 8E is another example medical image overlay 800*b* which includes the lower medical image 810L presented at the image location 812L. In this view, the eyewear device location 840 has changed, compared to the location 840 shown in FIG. 8D. The medical image 810L has been registered with the physical environment 600, as described herein. The image location 812L (e.g., location, orientation, and scale) is the same in FIG. 8E as it was in FIG. 8D. Accordingly, the medical image 810L is presented on the display 182B in a more angular orientation (and a slightly different scale) relative to its presentation in FIG. 8D. In this aspect, the image registration tool 912 and the localization system 915 (e.g., determining the current eyewear device location 840) cooperate to present a medical image overlay 800*a* that closely matches the location, orientation, and size of the real objects (e.g., the four real, lower teeth which were the subject of the medical image 810L) from any point of view.

The process of presenting the medical image overlay 800 in some implementations includes providing the user with one or more tools to adjust or otherwise configure the medical image overlay 800, as described herein, or to start and stop the presentation selectively. For example, the user may pause or stop (or re-start) the process of presenting the medical image overlay 800 by speaking a voice command, pressing a push button on the eyewear device 100, executing a hand gesture, or tapping a finger touch 681 on the touchpad 181.

The process of presenting the medical image overlay 800 in some implementations includes moving or otherwise adjusting the image location 812 relative to the target 50 such that the medical image 810, when registered, will be presented as an overlay in the foreground relative to the target 50. In this process, the overlay application 910 estimates the image location 812 (e.g., where the medical image overlay 800 is presented) relative to the target 50 (e.g., one or more teeth) based, in some implementations, on one or more marker locations 790. If all or part of the medical image overlay 800 is estimated to lie in the background relative to the target (e.g., behind the teeth), then the overlay application 910 moves or otherwise adjusts the image location 812 so the medical image 810 will be presented in the foreground relative to the target 50. IN some implementations, the overlay application 910 moves or otherwise adjusts the image location 812 automatically, without user input.

The image location 812 in some implementations is configurable, such that the process of presenting the medical image overlay 800 includes providing the user with one or more tools to adjust or otherwise configure the image location 812. The process of adjusting the image location 812 in some implementations includes calculating or adjusting the image location 812 based on the length and heading of a segment 521 traversed by a finger along a touchpad (as shown in FIG. 8D). The process of adjusting the image location 812 in some implementations includes identifying the original value of the image location 812 (e.g., as established when the registering the medical image, at block 706). The process of adjusting the image location 812 in some implementations includes calculating a new image location 812 based on the length and heading of the segment 521 (e.g., the longer the segment 521, the greater the change in the image location 812). The image location 812 in some implementations includes a sign (positive or negative) based on the heading of the segment 521 (e.g., move the image location 812 toward the foreground in response to a heading toward the front of the eyewear device 100; toward the background in response to a heading toward the ear). The process of adjusting the image location 812 in some implementations occurs in real-time so that the viewer can see the change in image location 812 as adjustments are made, and stop (e.g., lift the finger or execute a tap 681 on the touchpad 181) when the desired new image location 812 is reached.

Block 712 in FIG. 7 recites an example step of presenting the medical image overlay 800 in accordance with the field of view 904 associated with the camera 114B. In some implementations, the camera field of view 904, as shown in FIG. 8D, is larger than the display 182B. In this example step of presenting, the medical image overlay 800*a* appears when the image location 812L, 812U is detected within the field of view 904 of the camera 114B (e.g., based on the captured frames of video data 900). For example, referring to FIG. 8D, if the eyewear device 100 is moved very close to the upper teeth, so that the field of view 904 includes the upper image location 812U, then the upper medical image 810U will be presented on the display 182B. Conversely, if the field of view 904 does not includes the upper image location 812U, then the upper medical image 810U will not be presented on the display 182B.

In some implementations, a medical image overlay 800 includes a number of medical images (e.g., 810L, 810U, and in some cases many other images). This example step of presenting the medical image overlay 800 based on the field of view 904, in practice, means that the medical images will appear (or disappear) as the field of view 904 changes (e.g., as the eyewear device 100 moves through the physical environment 600).

Block 714 in FIG. 7 recites an example step of selectively adjusting a transparency value 820 associated with the medical image overlay 800. The transparency value 820 affects how much of the real objects are viewable when the medical image overlay 800 is presented on the display 182B (e.g., in the foreground relative to the real objects). In some implementations, the transparency value 820 is predefined (e.g., ten percent transparent, equivalent to ninety percent opaque).

The transparency value 820 in some implementations is configurable, such that the process of presenting the medical image overlay 800 includes providing the user with one or more tools to adjust or otherwise configure the transparency value 820. The process of adjusting the transparency value 820 in some implementations includes calculating or adjusting the transparency value 820 based on the length and heading of a segment 521 traversed by a finger along a touchpad (as shown in FIG. 8D). The process of adjusting the transparency value 820 in some implementations includes identifying the original value of the transparency value 820 (e.g., the default or predefined value). The process of adjusting the transparency value 820 in some implementations includes calculating a new transparency value 820 based on the length and heading of the segment 521 (e.g., the longer the segment 521, the greater the change in transparency). The transparency value 820 in some implementations includes a sign (positive or negative) based on the heading of the segment 521 (e.g., increase the transparency in response to a heading toward the front of the eyewear device 100; reduce for a heading toward the ear). The process of adjusting the transparency value 820 in some implementations occurs in real-time so that the viewer can see the change in transparency as adjustments are made, and stop (e.g., lift the finger or execute a tap 681 on the touchpad 181) when the desired transparency value 820 is reached.

The eyewear device 100 in some implementations includes a voice recognition module 925, as described herein, and a microphone 139 coupled to a speaker 191. The voice recognition module 925 in some implementations configures the processor 432 to perceive human speech, convert the received speech into frames of audio data, identify a first inquiry based on converted frames of audio data, and then perform an action in response to and in accordance with the identified first inquiry. For example, the human speech may include a verbal command (e.g., "transparency seventy percent") and, in response, the identified first inquiry causes the overlay application 910 to adjust the transparency value 820 as described herein.

Any of the functionality described herein for the eyewear device 100, the mobile device 401, and the server system 498 can be embodied in one or more computer software applications or sets of programming instructions, as described herein. According to some examples, "function," "functions," "application," "applications," "instruction," "instructions," or "programming" are program(s) that execute functions defined in the programs. Various programming languages can be employed to develop one or more of the applications, structured in a variety of manners, such as object-oriented programming languages (e.g., Objective-C, Java, or C++) or procedural programming languages (e.g., C or assembly language). In a specific example, a third-party application (e.g., an application developed using the ANDROID™ or IOS™ software development kit (SDK) by an entity other than the vendor of the particular platform) may include mobile software running on a mobile operating system such as IOS™ ANDROID™, WINDOWS® Phone, or another mobile operating system. In this example, the third-party application can invoke API calls provided by the operating system to facilitate functionality described herein.

Hence, a machine-readable medium may take many forms of tangible/non-transitory storage medium. Non-volatile storage media include, for example, optical or magnetic disks, such as any of the storage devices in any computer devices or the like, such as may be used to implement the client device, media gateway, transcoder, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code or data. Many of these forms of computer readable media may be involved in carrying one or more sequences of one or more instructions/program code to a processor for execution.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as plus or minus ten percent from the stated amount or range.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as a separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A method of presenting a medical image overlay with an eyewear device comprising a camera and a display, the method comprising:
   capturing frames of video data using the camera;
   storing a virtual marker comprising a marker location relative to a physical environment;
   registering a medical image associated with a target wherein the medical image comprises an image location relative to the marker location;
   determining an eyewear device location relative to the marker location based on the captured frames of video data; and
   presenting on the display a medical image overlay at the image location according to the eyewear device location, wherein the medical image overlay comprises the registered medical image, wherein the medical image overlay is associated with a selectively configurable transparency value and wherein the presenting comprises:
   generating the medical image overlay in accordance with the transparency value;
   detecting a segment traversed by a finger along a touchpad coupled to the eyewear device;
   adjusting the transparency value based on the detected segment; and
   applying the adjusted transparency value to the medical image overlay.

2. The method of claim 1, wherein the marker location is defined relative to a physical coordinate system, and wherein the step of registering the medical image further comprises:
   transforming the medical image according to the physical coordinate system, wherein the transforming comprises one or more of translation, rotation, and scaling.

3. The method of claim 1, wherein the medical image is associated with a film located in the background relative to the target, and wherein the step of registering the medical image further comprises:
   establishing the image location relative to the target such that the medical image overlay when presented at the image location will appear as an overlay in a foreground relative to the target.

4. The method of claim 1, wherein the step of presenting the medical image overlay further comprises:
   adjusting the image location relative to the target such that the medical image overlay when presented at the image location will appear as an overlay in a foreground relative to the target.

5. A method of presenting a medical image overlay with an eyewear device comprising a camera defining a field of view and a display, the method comprising:
   capturing frames of video data using the camera;
   storing a virtual marker comprising a marker location relative to a physical environment;
   registering a medical image associated with a target wherein the medical image comprises an image location relative to the marker location;
   determining an eyewear device location relative to the marker location based on the captured frames of video data; and
   presenting on the display a medical image overlay at the image location according to the eyewear device location, wherein the medical image overlay comprises the registered medical image, wherein the medical image overlay comprises a plurality of medical images comprising a first medical image associated with a first image location and a subsequent medical image associated with a subsequent image location, and where the presenting comprises:
   based on the captured frames of video data, determining whether the first image location is detected within the field of view;
   selectively presenting the first medical image in response to detecting the first image location;
   based on the captured frames of video data, determining whether the subsequent image location is detected within the field of view;
   disabling the presentation of the first medical image in response to not detecting the first image location within the field of view; and
   selectively presenting the subsequent medical image in response to detecting the subsequent image location.

6. An eyewear device for presenting a medical image overlay, comprising:
   a processor;
   a memory;
   a camera;
   a display; and
   programming in the memory, wherein execution of the programming by the processor configures the eyewear device to perform functions, including functions to:
   capture frames of video data using the camera;
   store a virtual marker comprising a marker location relative to a physical environment;
   register a medical image associated with a target wherein the medical image comprises an image location relative to the marker location;
   determine an eyewear device location relative to the marker location based on the captured frames of video data; and
   present on the display a medical image overlay at the image location according to the eyewear device location, wherein the medical image overlay comprises the registered medical image and wherein the function to present further comprises functions to:
   generate the medical image overlay in accordance with a transparency value;
   detect a segment traversed by a finger along a touchpad coupled to the eyewear device;
   adjust the transparency value based on the detected segment; and
   apply the adjusted transparency value to the medical image overlay.

7. The eyewear device of claim 6, wherein the function to register the medical image further comprises functions to:
   define the marker location relative to a physical coordinate system; and
   transform the medical image according to the physical coordinate system, wherein the transform function comprises one or more of translation, rotation, and scaling.

8. The eyewear device of claim 6, wherein the medical image is associated with a film located in the background relative to the target, and wherein the function to register the medical image further comprises functions to:
   establish the image location relative to the target such that the medical image overlay when presented at the image location will appear as an overlay in a foreground relative to the target.

9. The eyewear device of claim 6, wherein the function to present the medical image overlay further comprises functions to:
   adjust the image location relative to the target such that the medical image overlay when presented at the image location will appear as an overlay in a foreground relative to the target.

10. The eyewear device of claim 6, wherein the medical image comprises a plurality of medical images, comprising a first medical image associated with a first image location, wherein the camera defines a field of view, and wherein the function to present the medical image overlay further comprises functions to:
   based on the captured frames of video data, determine whether the first image location is detected within the field of view; and
   selectively present the first medical image in response to detecting the first image location.

11. A non-transitory computer-readable medium storing program code that, when executed, is operative to cause a processor of an eyewear device to perform the steps of:
- capturing frames of video data using a camera coupled to the eyewear device;
- storing a virtual marker comprising a marker location relative to a physical environment;
- registering a medical image associated with a target wherein the medical image comprises an image location relative to the marker location;
- determining an eyewear device location relative to the marker location based on the captured frames of video data; and
- presenting on a display of the eyewear device a medical image overlay at the image location according to the eyewear device location, wherein the medical image overlay comprises the registered medical image, and wherein the step of presenting comprises:
- generating the medical image overlay in accordance with a transparency value;
- detecting a segment traversed by a finger along a touchpad coupled to the eyewear device;
- adjusting the transparency value based on the detected segment; and
- applying the adjusted transparency value to the medical image overlay.

12. The non-transitory computer-readable medium storing program code of claim 11, wherein the program code when executed is operative to cause the processor to perform the further steps of:
- determining whether the medical image is associated with a film located in the background relative to the target;
- establishing the image location relative to the target such that the medical image overlay when presented at the image location will appear as an overlay in a foreground relative to the target; and
- adjusting the image location relative to the target such that the medical image overlay when presented at the image location will appear as an overlay in a foreground relative to the target.

13. A non-transit computer-readable medium storing program code that, when executed is operative to cause processor of an eyewear device to perform the steps of:
- capturing frames of video data using a camera coupled to the eyewear device;
- storing a virtual marker comprising a marker location relative to a physical environment;
- registering a medical image associated target wherein the medical image comprises an image location relative to the marker location,
- determining an eyewear device location relative to the marker location based on the captured frames of video data;
- presenting on a display of the eyewear device a medical image overlay at the image location according to the eyewear device location, wherein the medical image overlay comprises the registered medical image;
- determining whether the medical image overlay comprises a plurality of medical images, including a first medical image associated with a first image location;
- based on the captured frames of video data, determining whether the first image location is detected within a field of view associated with the camera;
- selectively presenting the first medical image in response to detecting the first image location
- determining whether the plurality of medical images further comprises a subsequent medical image associated with a subsequent image location;
- based on the captured frames of video data, determining whether the subsequent image location is detected within the field of view;
- disabling the presentation of the first medical image in response to not detecting the first image location within the field of view; and
- selectively presenting the subsequent medical image in response to detecting the subsequent image location.

* * * * *